United States Patent
Stankovic et al.

(10) Patent No.: US 10,022,042 B2
(45) Date of Patent: Jul. 17, 2018

(54) TISSUE AND CELLULAR IMAGING

(71) Applicants: Massachusetts Eye & Ear Infirmary, Boston, MA (US); Ecole Polytechnique Federale De Lausanne (EPFL), Lausanne (CH)

(72) Inventors: Konstantina Stankovic, Boston, MA (US); Demetri Psaltis, Preverenges (CH); Xin Yang, Renens (CH); Ye Pu, Ecublens (CH); Chia-Lung Hsieh, Erlangen (DE)

(73) Assignees: Massachusetts Eye & Ear Infirmary, Boston, MA (US); Ecole Polytechnique Federale De Lausanne (EPFL), Lausanne (CH)

( * ) Notice: Subject to any disclaimer, the term of this patent is extended or adjusted under 35 U.S.C. 154(b) by 156 days.

(21) Appl. No.: 14/354,690

(22) PCT Filed: Oct. 29, 2012

(86) PCT No.: PCT/US2012/062409
§ 371 (c)(1),
(2) Date: Apr. 28, 2014

(87) PCT Pub. No.: WO2013/063564
PCT Pub. Date: May 2, 2013

(65) Prior Publication Data
US 2014/0303504 A1  Oct. 9, 2014

Related U.S. Application Data

(60) Provisional application No. 61/552,913, filed on Oct. 28, 2011.

(51) Int. Cl.
*A61B 1/00* (2006.01)
*A61B 5/00* (2006.01)
(Continued)

(52) U.S. Cl.
CPC ............ *A61B 1/06* (2013.01); *A61B 1/00009* (2013.01); *A61B 1/00172* (2013.01);
(Continued)

(58) Field of Classification Search
None
See application file for complete search history.

(56) References Cited

U.S. PATENT DOCUMENTS 5,201,318 A * 4/1993 Rava .................... A61B 5/0059
600/476
5,438,989 A   8/1995 Hochman et al.
(Continued)

OTHER PUBLICATIONS

Campbell et al. 2010 Laryngoscope 120:1619-1624.*
(Continued)

*Primary Examiner* — Tse Chen
*Assistant Examiner* — Patrick M Mehl
(74) *Attorney, Agent, or Firm* — Fish & Richardson P.C.

(57) ABSTRACT

Systems and methods for imaging ear tissue include: directing illumination radiation to pass through an intact biological structure and be incident on ear tissue that does not include an exogenous fluorophore, at a plurality of locations, the illumination radiation including a plurality of light pulses each having a temporal duration of 500 femtoseconds or less; for each one of the plurality of locations, using a detector to detect radiation emitted from the location that passes through the intact biological structure; and forming an image of the tissue based on the detected radiation at each of the plurality of locations, where the emitted radiation corresponds to endogenous two-photon fluorescence of the tissue.

11 Claims, 10 Drawing Sheets

(51) Int. Cl.
*A61B 1/06* (2006.01)
*A61B 1/227* (2006.01)
*A61B 1/04* (2006.01)

(52) U.S. Cl.
CPC .............. *A61B 1/043* (2013.01); *A61B 1/227* (2013.01); *A61B 5/0071* (2013.01); *A61B 5/0066* (2013.01); *A61B 5/0068* (2013.01); *A61B 5/0084* (2013.01)

(56) References Cited

U.S. PATENT DOCUMENTS

| | | | |
|---|---|---|---|
| 8,099,156 | B1 | 1/2012 | Schnitzer et al. |
| 2002/0141714 | A1 | 10/2002 | Reed et al. |
| 2007/0038126 | A1* | 2/2007 | Pyle ..................... A61B 5/0059 600/476 |
| 2008/0017787 | A1 | 1/2008 | Shinichi et al. |
| 2009/0012406 | A1* | 1/2009 | Llewellyn ............ A61B 5/0062 600/478 |
| 2010/0262212 | A1 | 10/2010 | Shoham et al. |
| 2010/0317914 | A1 | 12/2010 | Puria et al. |
| 2011/0152602 | A1 | 6/2011 | Perkins et al. |
| 2011/0152744 | A1 | 6/2011 | Choi et al. |
| 2011/0152976 | A1 | 6/2011 | Perkins et al. |

OTHER PUBLICATIONS

Kim et al. 2008 J. Biomed. Optics 13:010501-1-010501-3.*
Levene et al. 2004 J. Neurophysiol. 91:1908-1912.*
Li et al. 2010 IEEE J. Select. Top. Quant. Electron. 16:516-523.*
Nikolenko et al. 2008 Frontiers in Neural Circuits 2:1-14.*
Tiede et al. 2007 J. Biomed. Opt. 12:021004-1-021004-8.*
Wang et al. 2009 J. Microscopy 238:1-20.*
Monfared et al. 2006 Otol. Neurotol. 27:144-152; Pub.Date Feb. 2006; manuscript 19 pages.*
Pogue et al. 2001 Photochem. Photobiol. 74: 817-824.*
Yang et al. 2013 SPIE Optical Metrology 2013, 2013, Munich, Germany, 87920T-1-87920T-7.*
Flusberg et al., "In vivo brain imaging using a portable 3.9 gram two-photon fluorescence microendoscope," Optics Letters, 30(17):2272-2274 (2005).
European Search Report issued in EP12844532 dated Jun. 19, 2015 (5 pages).
Ashkan Monfared et al "In Vivo Imaging of Mammalian Cochlear Blood Flow Using Fluorescence Microendoscopy" Otology & Neurotology, 2006, 27:144-152.
International Search Report and Written Opinion from corresponding application PCT/US2012/062409, dated Jan. 28, 2013, 11 pages.
Agarwal et al., "Scattering theory of distortion correction by phase conjugation," J. Opt. Soc. Am. 73(5): 529-537 (1983).
Balkany, "Endoscopy of the cochlea during cochlear implantation," Ann. Otol. Rhinol. Laryngol. 99: 919-921 (1990).
Bianchi et al., "A multi-mode fiber probe for holographic micromanipulation and microscopy," Lab Chip 12(3): 635-639 (2012).
Bird et al., "Two-photon fluorescence endoscopy with a micro-optic scanning head," Opt. Lett. 28(17), 1552-1554 (2003).
Cahalan et al., "Two-photon tissue imaging: Seeing the immune system in a fresh light," Nature Reviews Immunology 2(11): 872-880 (2002).
Campbell et al., "Flexible cochlear microendoscopy in the gerbil," Laryngoscope 120: 1619-1624 (2010).
Chaigneau et al., "Two-photon imaging of capillary blood flow in olfactory bulb glomeruli," Proc. Nat. Acad. Sci. 100(22): 13081-13086 (2003).
Chen et al., "In vivo imaging and low-coherence interferometry of organ of Corti vibration," J. Biomed. Opt. 12(2) (2007).
Cizmar et al., "Shaping the light transmission through a multimode optical fibre: complex transformation analysis and applications in biophotonics," Opt. Express 19(20): 18871-18884 (2011).
Coleman et al., "A protocol for cryoembedding the adult guinea pig cochlea for fluorescence immunohistology," J. Neurosci. Methods. 176: 144-51 (2009).
Conkey et al., "High-speed scattering medium characterization with application to focusing light through turbid media," Opt. Express 20(2): 1733-1740 (2012).
Cui et al., "Implementation of a digital optical phase conjugation system and its application to study the robustness of turbidity suppression by phase conjugation," Opt. Express 18(4): 3444-3455 (2010).
Denk et al., "Two-Photon Laser Scanning Fluorescence Microscopy," Science 248(4951): 73-76 (1990).
Dunning et al., "Demonstration of image transmission through fibers by optical phase conjugation," Opt. Lett. 7: 558-560 (1982).
Engelbrecht et al., "Ultra-compact fiber-optic two-photon microscope for functional fluorescence imaging in vivo," Opt. Express 16: 5556-5564 (2008).
Flusberg et al., "Fiber-optic fluorescence imaging," Nat. Methods 2(12): 941-950 (2005).
Fu et al., "Nonlinear optical endoscopy based on a double-clad photonic crystal fiber and a MEMS mirror," Opt. Express 14: 1027-1032 (2006).
Fu et al., "Second harmonic and sum frequency generation imaging of fibrous astroglial filaments in ex vivo spinal tissues," Biophys. J. 92(9): 3251-3259 (2007).
Hardie et al., "A new method for imaging and 3D reconstruction of mammalian cochlea by fluorescent confocal microscopy," Brain Res. 1000: 200-210 (2004).
Helmchen et al., "Deep tissue two-photon microscopy," Nature Methods 2(12): 932-940 (2005).
Hsieh et al., "Imaging through turbid layers by scanning the phase conjugated second harmonic radiation from a nanoparticle," Opt. Express 18(20): 20723-20731 (2010).
Jero et al., "A surgical approach appropriate for targeted cochlear gene therapy in the mouse," Hear. Res. 151: 106-114 (2001).
Jung et al., "Multiphoton endoscopy," Opt. Lett. 28: 902-904 (2003).
Li et al., "Imaging needle for optical coherence tomography," Opt. Lett. 25(20): 1520-1522 (2000).
MacDonald et al., "Three-dimensional imaging of the intact mouse cochlea by fluorescent laser scanning confocal microscopy," Hear Res. 243: 1-10 (2008).
Miller et al., "Two-photon imaging of lymphocyte motility and antigen response in intact lymph node," Science 296(5574): 1869-1873 (2002).
Myaing et al., "Fiber-optic scanning two-photon fluorescence endoscope," Opt. Lett. 31(8): 1076-1078 (2006).
Papadopoulos et al., "Focusing and scanning light through a multimode optical fiber using digital phase conjugation," Opt. Express 20(10): 10583-10590 (2012).
Paurisse et al., "Phase and amplitude control of a multimode LMA fiber beam by use of digital holography," Opt. Express 17(15): 13000-13008 (2009).
So et al., "Two-photon excitation fluorescence microscopy," Ann. Rev. Biomedical Engineering 2: 399-429 (2000).
Subhash et al., "Volumetric in vivo imaging of intracochlear microstructures in mice by high-speed spectral domain optical coherence tomography," J. Biomed. Optics 15(3): 036024 (2010).
Tiede et al., "Metabolic imaging of the organ of corti—a window on cochlea bioenergetics," Brain Research 1277: 37-41 (2009).
Tiede et al., "Determination of hair cell metabolic state in isolated cochlear preparations by two-photon microscopy," J. Biomed. Opt. 12: 021004 (2007).
Tomo et al., "Imaging the living inner ear using intravital confocal microscopy," Neuroimage 35: 1393-1400 (2007).
Vellekoop et al., "Exploiting disorder for perfect focusing," arXiv: 0910.0873v1, Oct. 5, 2009.
Vellekoop et al., "Exploiting disorder for perfect focusing," Nature Photonics 4: 320-322 (2010).
Vellekoop et al., "Scattered light fluorescence microscopy: imaging through turbid layers," Optics Letters 35(8): 1245-1247 (2010).

(56) References Cited

OTHER PUBLICATIONS

Wang et al., "Phase-sensitive optical coherence tomography imaging of the tissue motion within the organ of Corti at a subnanometer scale: a preliminary study," J. Biomed. Opt. 15: 056005 (2010).
Wang et al., "Two-photon microscopy of deep intravital tissues and its merits in clinical research," J. Microscopy 238(1): 1-20 (2010).
Wang et al., "Dynamics of noise-induced cellular injury and repair in the mouse cochlea," J. Assoc. Res. Otolaryngol. 3(3): 248-268 (2002).
Wong et al., "Optical coherence tomography of the rat cochlea," J. Biomed. Opt. 5: 367 (2000).
Wu et al., "Robust high-resolution OCT needle for side-viewing interstitial tissue imaging," IEEE J. Selected Topics in Quantum Electron. 66: 863-869 (2010).
Yaqoob et al., "Optical Phase Conjugation for Turbidity Suppression in Biological Samples," Nature Photonics 2(2): 110-115 (2008).
Zipfel et al., "Nonlinear magic: multiphoton microscopy in the biosciences," Nature Biotechnology 21(11): 1368-1376 (2003).
European Office Action issued in Application No. 12844532.7, dated Sep. 22, 2016.

\* cited by examiner

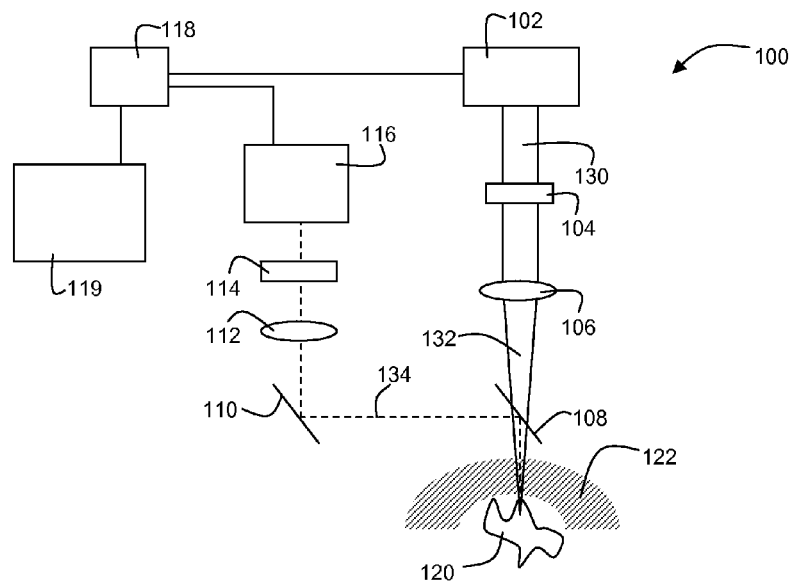
FIG. 1
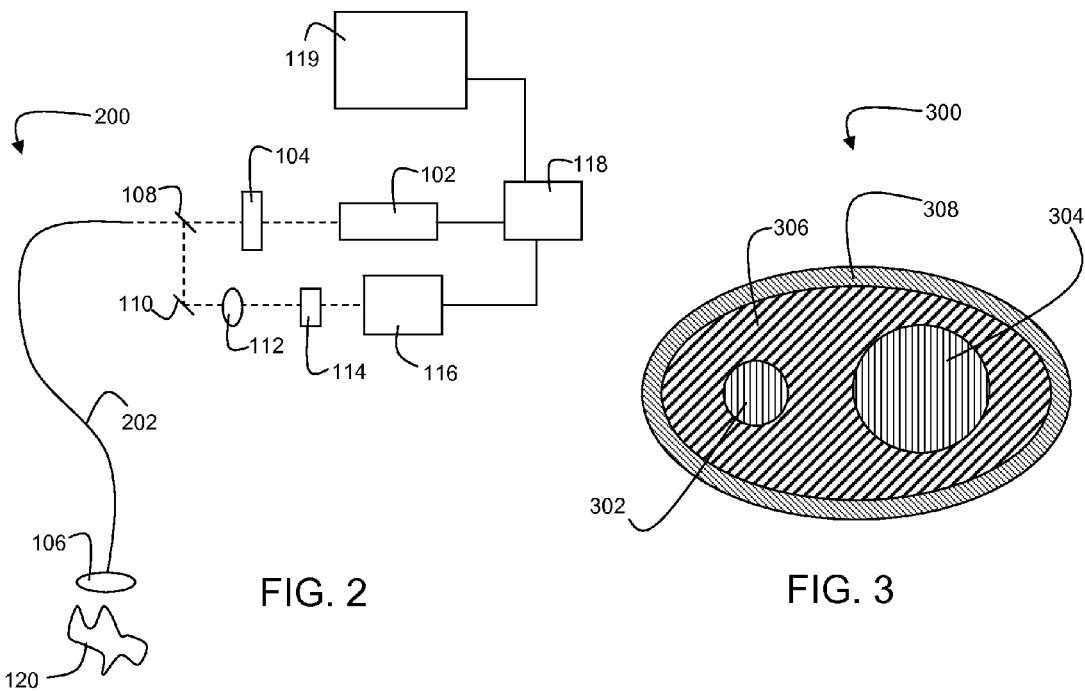
FIG. 2
FIG. 3

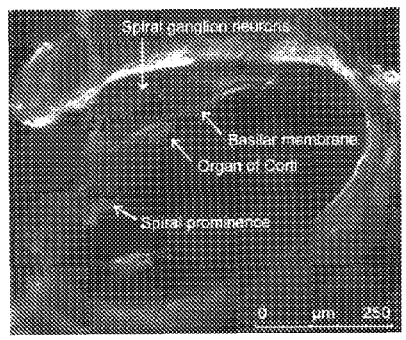
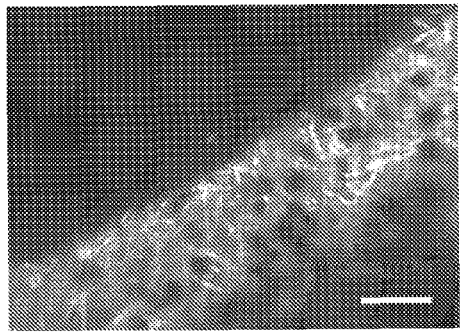
FIG. 6A  FIG. 6B
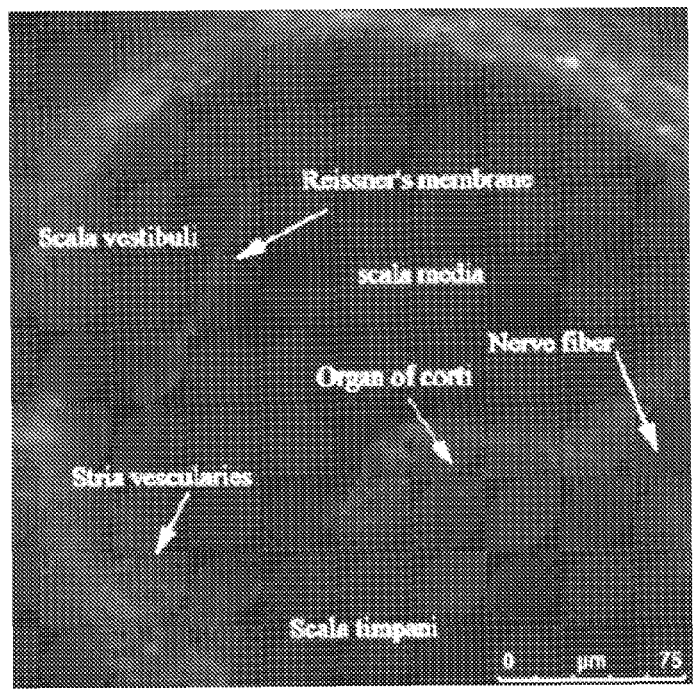
FIG. 7

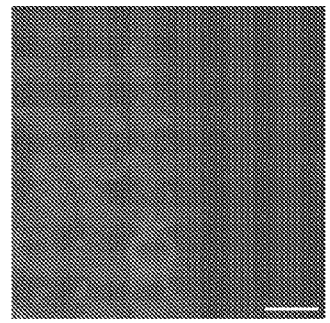
FIG. 15
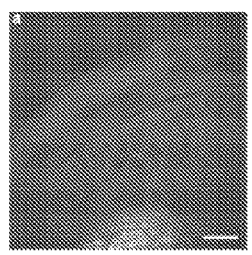 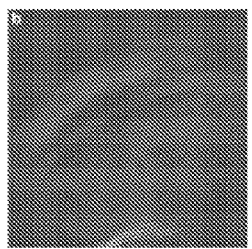 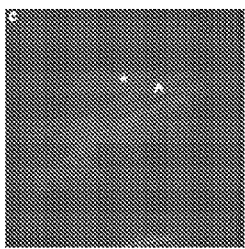 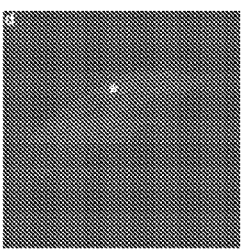
FIG. 16A   FIG. 16B   FIG. 16C   FIG. 16D
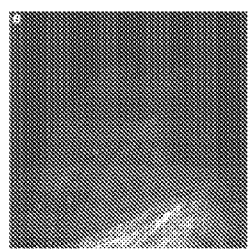 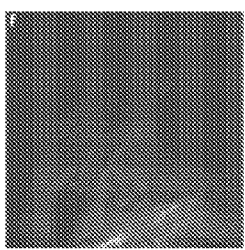 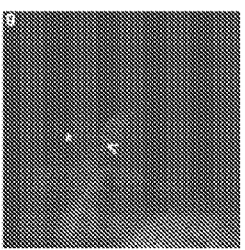 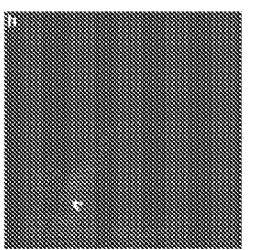
FIG. 16E   FIG. 16F   FIG. 16G   FIG. 16H

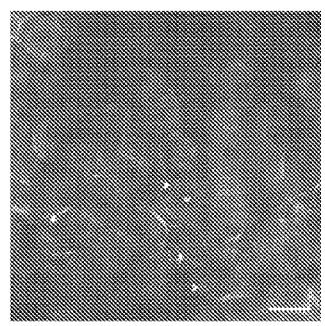
FIG. 17
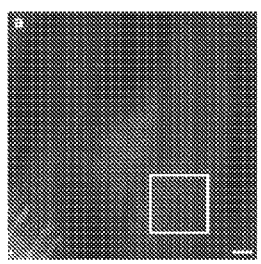 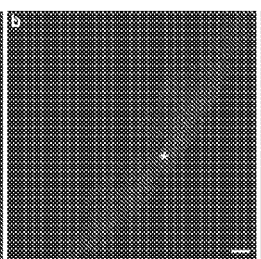 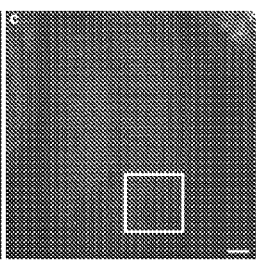 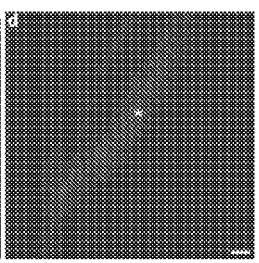
FIG. 18A  FIG. 18B  FIG. 18C  FIG. 18D
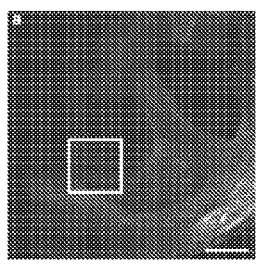 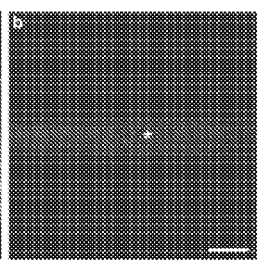 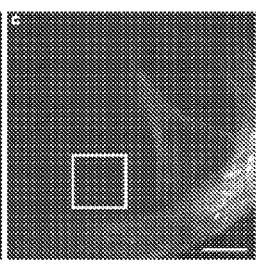 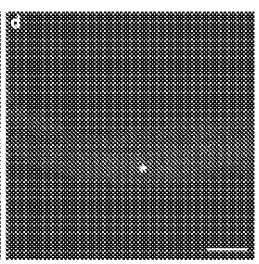
FIG. 19A  FIG. 19B  FIG. 19C  FIG. 19D

TISSUE AND CELLULAR IMAGING

CROSS-REFERENCE TO RELATED APPLICATIONS

This application is a national stage application under 35 U.S.C. § 371 of PCT Patent Application No. PCT/US2012/062409, filed on Oct. 29, 2012 and published as WO 2013/063564, which claims priority under 35 U.S.C. § 119 to U.S. Provisional Patent Application No. 61/552,913, filed on Oct. 28, 2011, the entire contents of which are incorporated herein by reference.

TECHNICAL FIELD

This disclosure relates to imaging of tissues and cells through a layer of bone or cartilage, and in particular to imaging inner ear cells encased in bone.

BACKGROUND

Hearing loss is the most common sensory deficit in the world, affecting almost 600 million people, and the most common congenital anomaly, affecting 2-6 per 1000 newborns. The most common type of hearing loss affects delicate mechanosensory and neural structures inside the inner ear, and is known as sensorineural hearing loss (SNHL). For the vast majority of people with SNHL the underlying cause is not known, because the inner ear cannot be biopsied at present without destroying hearing, and it is difficult to image cells (e.g., using techniques such as CT scanning and MRI) within the inner ear with sufficient resolution to establish diagnosis. Consequently, therapeutics are relatively crude and essentially limited to hearing aids and cochlear implants, which are prosthetics that are surgically inserted into the cochlea—the hearing part of the inner ear—to electrically stimulate residual neurons and bypass missing or nonfunctional cells. The performance of these devices varies widely, and the cellular origins of this variability are not well understood

SUMMARY

An important factor that limits the applicability of conventional bio-imaging techniques to the study of certain types of cells such as inner ear (e.g., cochlear) cells are the tissue structures surrounding the cells. For example, human cochlear cells, which are located in the cochlea of the inner ear, are surrounded by the hardest bone in the body. The human cochlea is also small in size and features small, narrow cochlear channels. Accordingly, human cochlear cells are typically not amenable to interrogation by many standard imaging techniques.

Disclosed herein are methods and systems that permit imaging and identification of a variety of hard-to-access cells and tissues in the human body, including inner ear hair cells and neurons. The methods and systems permit illumination radiation to be directed through a layer of bone, membrane, fibrous tissue, collagen, and/or cartilage and then be incident on the cells and tissues to be imaged. The wavelength of the radiation, and in some embodiments, the temporal and/or spatial distributions of the radiation, are selected to induce nonlinear responses in the cells that are illuminated. Such an arrangement is particularly advantageous, because given the difficulty of accessing the illuminated cells directly, staining of the cells in many situations is very difficult or impossible. Moreover, applying certain stains to cells may result in cell death. The methods and systems disclosed herein obviate these problems by permitting imaging of unstained tissues and cells based on nonlinear responses generated in the cells by the illumination radiation. Examples of nonlinear responses that can be generated using the methods and systems disclosed herein include two-photon fluorescence (TPF) emission and harmonic generation (HG), e.g., second harmonic generation (SHG). In some implementations of these methods, the system is configured to focus on autofluorescence due to flavin adenine dinucleotide (FAD).

The methods and systems disclosed herein also permit identification of damaged cells, such as inner ear cells, based on the measured TPF emission spectra of the cells. The cells can be illuminated through a layer of bone, or by inserting an endoscope into the inner ear via a natural opening such as a cochlear round window, or via a surgically made opening in the middle ear such as a stapedotomy or a cochleostomy), and the fluorescence emission spectra of the cells measured and compared to a standard emission spectrum to determine whether the cells are damaged.

In general, in a first aspect, the disclosure features methods for imaging unstained tissue hidden behind bone, membranes, collagen, and/or or cartilage. The methods include illuminating the unstained tissue by directing incident radiation to pass through a layer of bone or cartilage to be incident at a first location on the tissue, measuring radiation emitted from the unstained tissue, repeating the illuminating and measuring at a plurality of different locations on the tissue, and forming an image of the tissue based on the measurements of radiation emitted from the tissue resulting from illuminating the tissue at the plurality of different locations.

Embodiments of the methods can include any one or more of the following features.

The tissue can include cells, and the cells can be imaged. The layer of bone or cartilage can include cochlear bone. The cells can include at least one of inner ear neurons and inner ear hair cells. The illuminating can include directing a plurality of radiation pulses to be incident on the unstained tissue. A temporal duration of each of the radiation pulses is 500 fs or less (e.g., 100 fs or less).

Measuring the emitted radiation can include measuring radiation from the unstained tissue that corresponds to two-photon fluorescence emission from the tissue. Measuring the emitted radiation can include measuring radiation from the unstained tissue that corresponds to harmonic conversion of the radiation that is incident on the tissue. A frequency of the measured emitted radiation can be doubled relative to a frequency of the radiation that is incident on the tissue.

The methods can include selecting a central wavelength of the radiation that is incident on the unstained tissue to enhance two-photon fluorescence emission from the tissue, relative to illumination with white light. The methods can also include selecting a central wavelength of the radiation that is incident on the unstained tissue to enhance harmonic conversion of the incident radiation by the tissue, relative to illumination with white light. The central wavelength of the radiation can be, for example, between 400 nm and 1.5 microns, e.g., 500 nm and 1000 nm or 600 and 800 nm.

In some embodiments, the methods can include identifying boundaries of individual cells in the unstained tissue based on the emitted radiation. The methods can include identifying damaged cells within the unstained tissue based on the emitted radiation. In some embodiments, the methods can include identifying inner ear neurons and inner ear hair cells based on a central wavelength of the two-photon fluorescence emission.

In some aspects, the methods can include: generating illumination radiation using a radiation source; adjusting at least one of a temporal distribution and a spatial distribution of the illumination radiation based on radiation scattering properties of the layer of bone or cartilage; and using the adjusted illumination radiation to illuminate the unstained tissue. Adjusting at least one of a temporal distribution and a spatial distribution of the illumination radiation can include spatially dispersing frequency components of the illumination radiation, and modulating at least some of the dispersed frequency components using a spatial light modulator.

Illuminating the unstained tissue can include directing the radiation to pass through an endoscope from a proximal end to a distal end of the endoscope, where the endoscope is positioned so that the distal end is adjacent to the layer of bone or cartilage. Measuring radiation emitted from the unstained tissue can include positioning the endoscope so that the emitted radiation is coupled into the distal end of the endoscope and is measured at the proximal end.

The methods can include adjusting the at least one of a temporal distribution and a spatial distribution of the illumination radiation based on one or more properties of an endoscope through which the illumination radiation propagates before being incident on the unstained tissue.

Embodiments of the methods can also include any of the other features disclosed herein, in any combination, as appropriate.

In another aspect, the disclosure features methods for identifying damaged inner ear cells. These methods include: illuminating an inner ear cell located behind a bone with incident radiation; measuring a spectrum of radiation emitted through the bone from the illuminated inner ear cell to generate a measured emission spectrum; comparing the measured emission spectrum to a reference emission spectrum from an undamaged inner ear cell; and determining whether the inner ear cell is damaged based on the comparison between the measured and reference emission spectra. Embodiments of these methods can include any one or more of the following features.

The comparing can include determining a bandwidth of the measured emission spectrum, and comparing the determined bandwidth to a bandwidth for the reference emission spectrum. The inner ear cell may be determined to be damaged if the bandwidth of the measured emission spectrum differs from the bandwidth for the reference emission spectrum by 5% or more, e.g., 7.5% or more, 10% or more, or 15% or more.

Illuminating the inner ear cell with incident radiation can include directing the incident radiation to pass through a layer of bone before being incident on the inner ear cell. The incident radiation can include a plurality of radiation pulses, each pulse having a temporal duration of 500 fs or less, e.g., 400 fs or less, 300 fs or less, 250 fs or less, 200 fs or less, 150 fs or less, or 100 fs or less.

The measured spectrum of radiation emitted from the illuminated inner ear cell can include two-photon fluorescence emission from the illuminated inner ear cell, where the illuminated inner ear cell is unstained.

Illuminating the inner ear cell with radiation can include: generating illumination radiation using a radiation source; adjusting at least one of a temporal distribution and a spatial distribution of the illumination radiation based on radiation scattering properties of the layer of bone; and using the adjusted illumination radiation to illuminate the inner ear cell. Adjusting at least one of a temporal distribution and a spatial distribution of the illumination radiation can include spatially dispersing frequency components of the illumination radiation, and modulating at least some of the dispersed frequency components using a spatial light modulator.

Illuminating the inner ear cell with incident radiation can include using an endoscope to direct the incident radiation to pass through an opening in the bone.

Embodiments of the methods can also include any of the other features disclosed herein, in any combination, as appropriate.

In a further aspect, the disclosure features methods for imaging unstained tissue hidden behind bone or cartilage. These methods include: illuminating the unstained tissue by using an endoscope to direct incident radiation to pass through an opening in the bone or cartilage to be incident at a first location on the tissue; measuring radiation emitted from the unstained tissue; repeating the illuminating and measuring at a plurality of different locations on the tissue; and forming an image of the tissue based on the measurements of radiation emitted from the tissue resulting from illuminating the tissue at the plurality of different locations.

Embodiments of the methods can include any of the features disclosed herein, in any combination, as appropriate.

In another aspect, the disclosure features methods for imaging ear tissue that include: directing illumination radiation to pass through an intact biological structure and be incident on ear tissue that does not include an exogenous fluorophore, at a plurality of locations, the illumination radiation including a plurality of light pulses each having a temporal duration of 500 femtoseconds or less (e.g., 400 fs or less, 300 fs or less, 250 fs or less, 200 fs or less, 150 fs or less, or 100 fs or less); for each one of the plurality of locations, using a detector to detect radiation emitted from the location that passes through the intact biological structure; and forming an image of the tissue based on the detected radiation at each of the plurality of locations, where the emitted radiation corresponds to endogenous two-photon fluorescence of the tissue.

Embodiments of the methods can include any one or more of the following features.

The intact biological structure can include cochlear bone or cartilage. The intact biological structure can include a round window membrane of a cochlea that includes the ear tissue.

The image can include information corresponding to a thickness of the tissue of 10 microns or less. The image can include at least one of inner ear neurons and inner ear hair cells. The radiation emitted by the tissue includes radiation produced by harmonic conversion of the incident radiation.

The methods can include, prior to illuminating the tissue, selecting a central wavelength of the illumination radiation to increase an efficiency of the endogenous two-photon fluorescence of the tissue, relative to an efficiency of two-photon fluorescence emission induced by uniform exposure to a band of wavelengths from 400 nm to 800 nm, e.g., 500 to 700 nm. The methods can include, prior to illuminating the tissue, selecting a central wavelength of the illumination radiation to increase an efficiency of the harmonic conversion of the incident radiation, relative to an efficiency of harmonic conversion of the incident radiation induced by uniform exposure to a band of wavelengths from 400 nm to 800 nm. A central wavelength of the illumination radiation can be between 800 nm and 1.5 microns, e.g., between 900 nm and 1.3 microns or 1 micron and 1.2 microns.

The methods can include positioning an endoscope proximal to the round window membrane, using the endoscope to deliver the illumination radiation to the round window membrane, and using the endoscope to collect the emitted radiation emerging through the round window membrane, and to transport the emitted radiation to the detector. The methods can include identifying hair cells in the image, and assessing an extent of acoustically-induced damage in the tissue based on the identified hair cells. The methods can include identifying a plurality of cells of the tissue in the image, and determining whether each one of the plurality of cells is a neuron or a hair cell based on a central wavelength of a portion of the emitted radiation corresponding to the cell.

The methods can include identifying a cell in the image, measuring a spectrum of a portion of the emitted radiation corresponding to the cell to generate a measured emission spectrum for the cell, comparing the measured emission spectrum to a reference two-photon fluorescence emission spectrum for an undamaged cell, and determining whether the cell is damaged based on the comparison between the spectra. The comparing can include determining a bandwidth of the measured emission spectrum, and comparing the determined bandwidth to a bandwidth for the reference emission spectrum. The cell can be determined to be damaged if a difference between the bandwidths of the measured and reference emission spectra is 5% or more, e.g., 10% or more, or 15% or more.

The methods can include: repeating some or all of the above steps to form a plurality of successive images of the tissue; after forming each one of the successive images, directing the illumination radiation to a different plurality of locations so that a next one of the successive images includes contributions from a different region of the tissue; and combining the plurality of successive images to form a three-dimensional image of the tissue. The methods can include translating an endoscope that transports the illumination radiation to direct the illumination radiation to a different plurality of locations. The methods can include adjusting one or more optical elements to direct the illumination radiation to a different plurality of locations.

Embodiments of the methods can also include any of the other features disclosed herein, in any combination, as appropriate.

In a further aspect, the disclosure features systems for imaging ear tissue that include a radiation source configured to generate illumination radiation that includes radiation pulses having a temporal duration of 500 femtoseconds or less, a detector configured to detect radiation emitted from the tissue, and an electronic processor configured to: direct illumination radiation generated by the radiation source to pass through an intact biological structure and be incident on ear tissue that does not include an exogenous fluorophore, at a plurality of locations; for each one of the plurality of locations, use the detector to measure radiation emitted from the location that passes through the intact biological structure; and form an image of the tissue based on the detected radiation at each of the plurality of locations, where the emitted radiation corresponds to endogenous two-photon fluorescence of the tissue.

Embodiments of the systems can include any one or more of the following features.

The system can be configured to image through an intact biological structure such as cochlear bone or cartilage and/or a round window membrane or oval window of a cochlea.

The systems can include an optical sub-system configured to focus the illumination radiation onto the tissue, and the electronic processor can be coupled to the optical sub-system and configured to adjust a focal distance of the optical sub-system. The systems can include an endoscope coupled to the radiation source and the detector, and the electronic processor can be configured to adjust a position of the endoscope relative to the intact biological structure.

The systems can include a spatial light modulator, and the electronic processor can be configured to adjust the spatial light modulator to compensate for at least one of temporal, spatial, and polarization distortion of the incident radiation as it passes through the intact biological structure.

The detector can be a spectral detector, and the electronic processor can be configured to identify a cell in the image, measure a spectrum of a portion of the emitted radiation corresponding to the cell to generate a measured emission spectrum for the cell, compare the measured emission spectrum to a reference two-photon fluorescence emission spectrum for an undamaged cell, and determine whether the cell is damaged based on the comparison between the spectra.

The electronic processor can be configured to: form a plurality of successive images of the tissue based on radiation emitted from the tissue; after forming each one of the successive images, adjust one or more optical elements to change a focal distance of the illumination radiation in the tissue so that a next one of the successive images includes contributions from a different region of the tissue; and combine the plurality of successive images to form a three-dimensional image of the tissue.

Embodiments of the systems can also include any of the other features disclosed herein, in any combination, as appropriate.

The disclosure also encompasses systems and devices for carrying out the various methods, e.g., as illustrated in FIGS. 1 and 2 and described herein.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the subject matter disclosed herein, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

As used herein, an "unstained cell" or "unstained tissue" refers to a cell or tissue to which no exogenous fluorophore (e.g., a biological stain or a fluorescent tag or marker) has been added, and which has not been genetically modified to express a fluorescent marker or chemical moiety (such as green fluorescent protein, for example).

The details of one or more embodiments are set forth in the accompanying drawings and the description below. Other features and advantages will be apparent from the description, drawings, and claims.

DESCRIPTION OF DRAWINGS

FIG. 1 is a schematic diagram showing an embodiment of a system for imaging tissues and cells.

FIG. 2 is a schematic diagram showing another embodiment of a system for imaging tissues and cells.

FIG. 3 is a schematic cross-sectional diagram of an endoscopy fiber.

FIG. 6A is an image of a mouse cochlea.

FIG. 6B is an image of a human cochlea.

FIGS. 7, 8A, and 8B are images of a nine week old normal cochlea imaged through the encasing bone.

FIG. 15 is a two-photon fluorescence image of an unfixed cochlea obtained within 5 minutes of cochlear extraction from a mouse ear.

FIG. 16A is a maximum intensity projection of a three-dimensional stack of images of a hook region of the organ of Corti in a sample mouse cochlea that was not acoustically overexposed.

FIGS. 16B-16D are two-photon fluorescence images of the sample shown in FIG. 16A, each image corresponding to a different cross-sectional plane through the sample.

FIG. 16E is a maximum intensity projection of a three-dimensional stack of two-photon fluorescence images of a hook region of the organ of Corti in a sample mouse cochlea that was acoustically overexposed.

FIGS. 16F-16H are two-photon fluorescence images of the sample shown in FIG. 16E, each image corresponding to a different cross-sectional plane through the sample.

FIG. 17 is a two-photon fluorescence image of cochlear neurons in a sample obtained by imaging directly through the cochlear bone.

FIG. 18A is a maximum intensity projection of a three-dimensional stack of two-photon fluorescence images of the upper basal turn of a sample mouse cochlea that was not acoustically overexposed.

FIG. 18B is a high-magnification image of the region of the upper basal turn shown in FIG. 18A.

FIG. 18C is a maximum intensity projection of a three-dimensional stack of two-photon fluorescence images of the upper basal turn of a sample mouse cochlea that was acoustically overexposed.

FIG. 18D is a high-magnification image of the region of the upper basal turn shown in FIG. 18C.

FIG. 19A is a maximum intensity projection of a three-dimensional stack of two-photon fluorescence images of the apical turn of a sample mouse cochlea that was not acoustically overexposed.

FIG. 19B is a high-magnification image of the region of the apical turn shown in FIG. 19A.

FIG. 19C is a maximum intensity projection of a three-dimensional stack of two-photon fluorescence images of the apical turn of a sample mouse cochlea that was acoustically overexposed.

FIG. 19D is a high-magnification image of the region of the apical turn shown in FIG. 19C.

Like reference symbols in the various drawings indicate like elements.

DETAILED DESCRIPTION

Figure 4A:
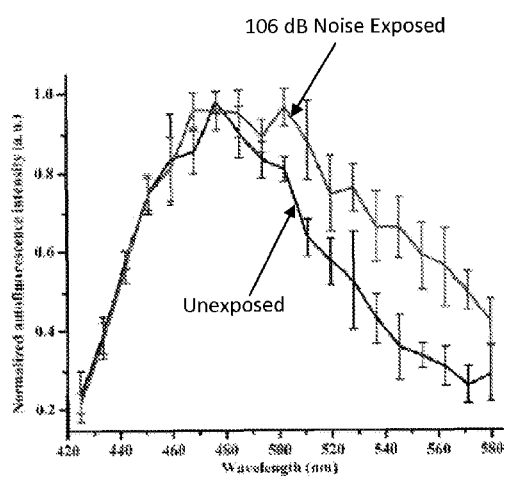
FIG. 4A is a graph showing emission spectra for hair cells before and after exposure to traumatic noise.

As discussed briefly above, the systems and methods disclosed herein can be used to image and identify tissues and cells, and even to identify damaged tissues and cells, based on tools of nonlinear optics, including shifts in emission spectra. The cells can be imaged through layers of bone and other hard tissues encasing the tissues and cells. Alternatively, or in addition, the cells can be imaged through one or more natural openings into the cochlea such as the round window, using an optical fiber inserted into the inner ear. All of these images have a resolution sufficient to identify and observe individual cells within a tissue. The first part of this disclosure discusses imaging systems that can be used to obtain cell images, and the second part of this disclosure discusses methods for obtaining images and performing cellular identification.

Imaging Systems

FIG. 1 is a schematic diagram of an embodiment of an imaging system 100 configured to acquire images of tissues and cells that are surrounded by hard tissues such as bone by imaging the cells directly through the bone, and without the need for staining the cells. System 100 includes a radiation source 102, an optional spatial light modulator 104, focusing optics 106, a beamsplitter 108, a reflecting mirror 110, radiation collecting optics 112, a filter 114, and a detector 116. As shown in FIG. 1, illumination radiation 130 is generated by radiation source 102, passes through spatial light modulator 104 and focusing optics 106, and is focused through a layer of bone 122 onto tissue cells 120 as incident radiation 132. Emitted radiation 134 from tissue cells 120 emerges through the layer of bone 122, is reflected by beamsplitter 108 and mirror 110, is collected by radiation collecting optics 112 and filtered by filter 114, and then is incident on detector 116.

Radiation source 102 can include any one or more of a variety of different radiation sources, including CW and pulsed lasers, flash lamp-based sources, LED-based sources, and laser diode-based sources. In some embodiments, radiation source 102 generates a plurality of radiation pulses that form illumination radiation 130. The radiation pulses can be ultra-short laser pulses, each having a temporal duration (e.g., a full-width a half-maximum temporal duration) of 1 ps or less (e.g., 750 fs or less, 500 fs or less, 200 fs or less, 100 fs or less, 50 fs or less).

In general, illumination radiation 130 includes a band of spectral frequencies. The spectral bandwidth of illumination radiation 130 can generally be varied as desired (e.g., by adjusting source 102), and may vary according to the temporal duration of radiation pulses in illumination radiation 130. For example, the full-width at half-maximum spectral bandwidth of radiation pulses in illumination radiation 130 can be 1 nm or more (e.g., 5 nm or more, 15 nm or more, 25 nm or more, 35 nm or more, 50 nm or more, 80 nm or more). The central wavelength of the spectral bandwidth can also generally be adjusted as desired. The central wavelength can be adjusted, for example, to modulate the strength of a nonlinear response induced in tissue cells 120 when they are exposed to incident radiation 132. In general, the central wavelength of illumination radiation 130 can be in the ultraviolet, visible, or infrared region of the electromagnetic spectrum. For example, the central wavelength can be between 400 nm and 500 nm, between 500 nm and 600 nm, between 600 nm and 700 nm, between 700 nm and 800 nm, between 800 nm and 1000 nm, between 1000 nm and 1200 nm, between 1200 nm and 1500 nm, and/or greater than 1500 nm.

Optional spatial light modulator 104 can be used to adjust the temporal and/or spatial distribution of illumination radiation 130. For example, in some embodiments, spatial light modulator 104 includes a first dispersive element (such as a diffraction grating) to spatially disperse frequency components of illumination radiation 130. The spatially dispersed frequency components are then incident on a radiation modulating element such as a liquid crystal mask, which can adjust one or more of the intensity, phase, and polarization of the individual frequency components. The modulated frequency components are then recombined by a second dispersive element (e.g., another diffraction grating) to form incident radiation 132. A wide variety of systems can be implemented as spatial light modulator 104. Exemplary systems and methods are disclosed, for example, in U.S. Pat. No. 5,719,650, the entire contents of which are incorporated herein by reference.

Spatial light modulator 104 can also include one or more filter elements that adjust the spectral properties (e.g., the central wavelength, the spectral bandwidth, and/or the distribution of spectral frequencies) and/or the spatial properties and/or the polarization properties of illumination radiation 130. Exemplary filter elements that can be used in spatial light modulator 104 include bandpass filters, neutral density filters, line filters, notch filters, apertures, waveplates, polarizers, and optical retarders.

Focusing optics 106 include one or more lenses and mirrors (refractive and/or reflective) that direct incident radiation 132 through beamsplitter 108 and focus the incident radiation through bone layer 122 and onto tissue cells 120. The focal lengths, sizes, and geometry of the various elements in focusing optics 106 are generally selected to focus incident radiation 132 to a small spot (e.g., 20 microns or less, 10 microns or less, 5 microns or less) on the surface of cells 120. In some embodiments, for example, where incident radiation 132 includes ultra-short radiation pulses with durations less than about 250 fs, the elements of focusing optics 106 are also selected to ensure that the durations of the pulses do not increase significantly as the pulses pass through focusing optics 106. For example, focusing optics 106 can include reflective lenses, which are typically less dispersive than refractive lenses.

Emitted radiation 134 is received by radiation collecting optics 112, which collimate (or at least partially collimate) the emitted radiation into a beam. Radiation collecting optics 112 can generally include lenses, mirrors, and any of the other elements disclosed above in connection with focusing optics 106.

Emitted radiation 134 then passes through filter 114, which is configured to adjust the spectral properties of the emitted radiation. In particular, filter 114 can be configured to filter out wavelengths of light in emitted radiation 134 that correspond to wavelengths present in incident light 132. For example, in some embodiments, incident radiation 132 includes a band of spectral wavelengths centered at a wavelength $\lambda_1$, and emitted radiation 134 includes a first spectral band centered at a wavelength $\lambda_1$ (corresponding to the incident radiation) and a second spectral band centered at a wavelength $\lambda_2$ (corresponding to emitted light from tissue cells 120). Filter 114 can include filter elements that filter out the first spectral band from emitted radiation 134 and allow the second spectral band to pass through filter 114.

The filtered emitted radiation 134 is then incident on detector 116, which measures the intensity of the radiation. A variety of different types of detectors can be implemented in detector 116, including CCD detectors, CMOS-based detectors, photodiodes, photon counters, and photomultiplier tubes. In addition, detector 116 can include a variety of different types of signal amplifiers, including lock-in amplifiers, dynodes, and microchannel plates.

In some embodiments, detector 116 can include wavelength-selective detectors such as spectrometers and/or monochromators. Where detector 116 can be tuned to selectively measure emitted radiation 134 in a particular wavelength band, filter 114 may not be present in system 100 (e.g., detector 116 can perform functions similar to filter 114).

System 100 in FIG. 1 can generally be configured in a variety of ways. In some embodiments, for example, system 100 is configured as a microscope (e.g., a confocal microscope). In other embodiments, system 100 can be configured as a bench-top or mobile imaging system, for example.

To acquire images of cells 120, incident light 132 is scanned sequentially from point-to-point on the surface of the cells, and emitted light 134 from tissue cells 120 is detected following each sequential illumination. A variety of different methods can be used to translate incident light 132 from one location to another on the surface of the tissue. In some embodiments, for example, one or more of the elements in focusing optics 106 (e.g., one or more mirrors and/or lenses) is translated or rotated to change the optical path of incident light 132, thereby deflecting the incident light from one point to another. In certain embodiments, radiation source 102, spatial light modulator 104, and/or focusing optics 106 are translated relative to tissue cells 120 to scan the illumination spot formed by incident light 132 across the surface of tissue cells 120. Still further, in some embodiments, the entire system 100 is translated relative to tissue cells 120. Relative translation can be accomplished either by physically displacing system 100, or by mounting tissue cells 120 on a movable stage and physically displacing tissue cells 120 while system 100 remains fixed in position.

At each location where tissue cells 120 are illuminated with incident light 132, the tissue cells emit light in response to the illumination (e.g., emitted light 134). In general, emitted light 134 is not spatially resolved by system 100. Instead, emitted light 134 is collected and measured as if the emitted light arose from a single point on the surface of tissue cells 120. Thus, by illuminating and measuring emitted light at a large number of closely-spaced locations on the surface of tissue cells 120, an image of tissue cells 120 can be created. Because the tissue cells are not imaged directly through bone layer 122, the bone layer—which typically strongly scatters both incident and emitted radiation—does not impede image formation. To the contrary, images of tissue cells 120 can be obtained at relatively high resolution (e.g., a resolution of 1.0 micron, or even 0.5 micron, or smaller), where "resolution" refers to the smallest feature in an image that can be optically resolved. In this manner, system 100 permits high resolution images of individual cells to be obtained and displayed to a system operator (e.g., via a display coupled to detector 116, which is not shown in FIG. 1).

System 100 can also include an electronic processor 118 and a display 119. Electronic processor can be configured to display a variety of system and image information to an operator via display 119, including images obtained by detector 116. More generally, electronic processor 118 can be configured to perform any or all of the steps disclosed herein, individually or in any combination, for obtaining tissue images. For example, electronic processor 118 can be configured to adjust various operating parameters of radiation source 102, to adjust the configuration of spatial light modulator 104, to adjust one or more elements of focusing optics 106 and/or radiation collecting optics 112, to adjust filter 114 to select a particular wavelength pass band, and/or to operate detector 116 to detect light emitted from tissues. Electronic processor 118 can also receive measurement information from detector 116 and, on the basis of this information, can form images of tissue.

FIG. 2 shows an embodiment of another imaging system 200 for obtaining images of cells. Imaging system 200 can be used to obtain cell images through hard tissues such as bone and cartilage. Alternatively, imaging system 200 can also be used to image cochlear cells through one or more natural openings in the cochlea such as the round window, which is discussed further below. In FIG. 2, elements that are the same as the elements in FIG. 1 are shown with the same reference numbers. System 200 includes an endoscope 202 that is configured both to deliver incident radiation 132 to tissue cells 120, and to deliver emitted radiation 134 from tissue cells 120 to detector 116. To achieve this dual functionality, endoscope 202 includes an optical fiber arrangement that is configured for two-way transmission of radiation. Such an optical fiber can also be inserted into the inner ear directly, bypassing the encasing bone. Typically, fibers used in this manner have the same diameter as cochlear implants (which can themselves be inserted into the cochlea without destroying residual hearing).

A variety of different optical fiber arrangements are possible in endoscope 202. In some embodiments, endoscope 202 includes a single optical fiber, which can be a single mode fiber or a multimode fiber. Multimode fibers, in general, have larger core sizes, and coupling radiation into such fibers is easier than for single mode fibers. However, single mode fibers can be designed so that they are less dispersive than multimode fibers. In general, both types of fibers can be used in the systems and methods disclosed herein.

In some embodiments, the fiber arrangement in endoscope 202 can include multiple fibers. For example, FIG. 3 shows a schematic cross-sectional diagram of an endoscope fiber arrangement 300 that includes two fibers, a delivery fiber 302 for incident radiation 132 and a receiving fiber 304 for emitted radiation 134. Both delivery fiber 302 and receiving fiber 304 are surrounding by a cladding 306 and a sheath 308. In FIG. 3, delivery fiber 302 is a small-core single mode fiber selected to minimize dispersion of the radiation pulses in incident radiation 132, whereas receiving fiber 304 is a large-core multimode fiber that facilitates coupling of emitted radiation 134 into the fiber. More generally, however, either or both of the fibers can be single-mode or multimode. Further, endoscope fiber arrangement 300 can generally include any number of fibers, arranged in any geometry, based on a variety of factors such as light collection efficiency and the overall size requirements for endoscope 202.

In certain embodiments, the fiber arrangement in endoscope 202 can also act as a filter. For example, certain processes that lead to emission of light from tissue cells 120 have a strong polarization dependence, so that if incident light 132 is linearly polarized in a particular direction, emitted light 134 may have relatively well-defined polarization properties (e.g., it may be linearly polarized along the same or another direction). When the polarization properties of incident light 132 and emitted light 134 are different, fibers in endoscope 202 can be used to discriminate between the two. For example, the fiber that receives emitted light 134 in endoscope 202 can be a polarization-selective fiber oriented to match the polarization of emitted light 134, so that emitted light 134 is coupled into the fiber, but incident light 132 (which does not match the fiber's polarization orientation) is effectively filtered out by the fiber. This arrangement allows a relatively high intensity of incident light 132 to be delivered to tissue cells 120, while at the same time ensuring that the amount of backscattered and/or reflected incident light that reaches detector 116 is relatively small or non-existent.

To perform point-to-point scanning of incident light 132 in FIG. 2, the same methods disclosed above in connection with FIG. 1 can be used. Other methods are also possible by taking advantage of the flexible nature of endoscope 202. For example, endoscope 202 can be translated relative to tissue cells 120 to deliver incident light 132 at particular locations on the surface of the cells. Translations of endoscope 202 can be performed, for example, by a fiber translation stage (not shown in FIG. 2) coupled to the endoscope. Such stages permit very fine position adjustments of fibers, with resolutions of 1.0 micron or less, or even 500 nm or less.

A variety of different types of endoscopes can be used in system 200. In some embodiments, for example, scanning fiber endoscopes developed for optical coherence tomography (OCT) imaging can be used. The endoscopes used can have a thickness of 3 mm or less (e.g., 2 mm or less, 1 mm or less, 500 microns or less). Certain endoscopes are configured for side-viewing; these are especially useful for imaging the core component of the cochlea—the Organ of Corti—where the sensory cells reside. Suitable commercially available endoscopes include the C7-XR™ OCT Intravascular Imaging System (available from St. Jude Medical Inc., St. Paul, Minn.).

In some embodiments, where system 200 includes an endoscope translator (e.g., a fiber translation stage), electronic processor 118 can be coupled to the translator to position the endoscope relative to the tissue being imaged. Translation of the endoscope can occur along one or more of three orthogonal coordinate axes.

Imaging and Identification Methods

The systems discussed in the previous section permit a wide variety of different methods that can be used to measure emitted light from tissues (collectively) and cells (individually) to be performed. The methods disclosed herein, however, can be used to acquire images of tissues and cells in conditions that might not otherwise be possible with conventional imaging techniques. In particular, as explained briefly above, certain types of tissue cells such as inner ear neurons and hair cells are encased within a layer of hard bone in the body. Accessing such tissue cells, either for purposes of staining or imaging, is difficult and invasive.

The methods disclosed herein use nonlinear optical responses generated in tissues of interest by excitation radiation to achieve high resolution imaging of tissue cells encased in a layer of bone or other relatively hard tissue such as cartilage, or opaque or translucent membranes, such as the round window of the cochlea. The tissue cells are unstained; the light emitted from the tissue cells arises from nonlinear optical interactions between endogenous moieties within the tissue and the excitation radiation.

In general, the intensity of radiation emitted as a result of a nonlinear optical wave mixing process scales as a product of the intensities of the excitation field(s). Thus, for example, for a second order nonlinear process, the intensity of the emitted radiation scales with the square of the intensity of the excitation field. As a result, appreciable emitted radiation is only observed where excitation field strengths are very high. Typically, lasers (and particularly ultrafast lasers with pulse durations of 250 fs or less, and even 100 fs or less) are used to induce nonlinear optical responses owing to their extremely high localized field strengths.

Even within the spatial and temporal profile of an ultrashort laser pulse, however, the fields required to induce nonlinear optical responses in most biological structures are only present at the peak of the pulse (in both space and time). As a result, when such pulses are incident on a biological structure, nonlinear responses are typically induced only at a spot in the structure that corresponds to the position of the pulse peak. As a result, nonlinear optical processes—when used for imaging—can effectively "section" a sample in three dimensions, and restrict the effective region from which a sample response is measured to a very small portion of the sample—much smaller than the minimum spot size of the pulse on the sample. As a result, induced nonlinear optical responses present a possible route to obtaining extremely high resolution images of biological structures, including cells.

In the systems and methods disclosed herein, due to the effective sectioning discussed above, two dimensional images of tissues typically include contributions from relatively small thicknesses of tissue. For example, images can include contributions from tissue thicknesses of 25 microns or less (e.g., 20 microns or less, 15 microns or less, 10 microns or less, 5 microns or less, 2 microns or less).

Among the variety of different nonlinear optical responses that can be induced in tissues, the inventors have discovered that two techniques are particularly well suited to the imaging of inner ear cells through overlying bone. The first such technique is two-photon fluorescence (TPF). In TPF, a moiety within a biological structure of interest absorbs two photons from a pulse of excitation radiation, and emits a single photon via fluorescence. Unlike single-photon fluorescence (SPF) in which the wavelength of the emitted photon is longer than the wavelength of the incident photon, in TPF the wavelength of emitted photon is typically shorter than the wavelengths of the two absorbed photons. As a result, TPF signals are relatively easy to distinguish spectrally from SPF and excitation radiation signals, even though they are generally weaker in intensity. Additional aspects of the measurement of TPF signals are disclosed, for example, in F. Helmchen, "Deep tissue two-photon microscopy," Nature Methods 2: 932-940 (2005), the entire contents of which are incorporated by reference herein.

The second technique is harmonic generation, e.g., second-harmonic generation (SHG). In SHG, two photons of frequency f mix in a nonlinear optical medium (e.g., a moiety within a biological structure of interest) to generate a single photon of frequency 2f. Unlike TPF, SHG is not an absorption-emission process in the biological structure, but a wave-mixing process. As such, while this disclosure refers to radiation "emitted" as a result of SHG, it is to be understood that "emission" in this context refers to the process by which second harmonic radiation is generated.

Typically, biological molecules and entities have small nonlinear susceptibilities. As a result, the intensity of light emitted as a result of induced TPF and SHG responses is relatively small. Nonetheless, a variety of detectors (described in the previous section) can be used to measure the emitted light. At the same time, the induced TPF and SHG responses are similar to other nonlinear optical responses in that emission of light only occurs from the center-most region of the excitation radiation spot. As a result, images based on measured radiation emitted from TPF and SHG responses can have very high optical resolution in three dimensions.

The choice of the central wavelength of the excitation radiation can strongly influence the amount of radiation emitted in TFP and SHG interactions. TPF is a resonance interaction, and the amount of radiation emitted is strongest when the two photons that are absorbed match a two-photon absorption transition for the absorbing moiety. Thus, the amount of radiation emitted via TPF in a sample can be increased (relative to white light illumination of the same sample in which the same number of photons are distributed equally throughout the visible region of the spectrum in the excitation radiation) by tuning the central wavelength of the excitation radiation to match a two-photon transition in the sample. Biological systems are typically chemically complex and have multiple species capable of undergoing TPF. As a result, wavelength tuning of the excitation radiation can be used to selectively interrogate a variety of different types of tissues and/or cells, and even specific entities within the tissues. For inner ear cells, for example, it has been determined that excitation radiation at a central wavelength of approximately 800 nm appears to provide the strongest contrast (e.g., difference in intensity of TPF emission) between damaged and healthy cells.

SHG is not a resonance interaction in the absorptive sense, but the nonlinear susceptibility of individual moieties in biological systems is also strongly wavelength dependent. Accordingly, the amount of radiation emitted via SHG can also be increased (relative to white light illumination) by tuning the central wavelength of the excitation radiation to match the maximum of a particular entity's nonlinear susceptibility. As biological systems also typically include multiple species capable of participating in SHG interactions, wavelength tuning can also be used to selectively interrogate different species within tissues.

Although this disclosure focuses primarily on TPF and SHG, a variety of other nonlinear optical responses can be induced (and the emitted light measured and used to form images) in tissues of interest. Exemplary interactions that can be exploited include third harmonic generation, sum- and difference-frequency mixing, and three-photon fluorescence.

(a) Imaging Through Intact Bone and Hard Tissue

When nonlinear optical interactions are induced in tissue cells by directing excitation radiation to pass through bone or other opaque tissue, e.g., hard and/or fibrous tissue, to reach the cells, and the (relatively weak) radiation emitted as a result of such interactions is measured, the bone or other hard tissue (which is relatively dense) operates as a broadband radiation scattering medium. Scattering of radiation by bone and other hard tissue is an important consideration for two reasons. First, the relatively weak emitted radiation will be scattered to a certain extent, making it harder to detect. Second, the excitation radiation will also be scattered to some extent before it reaches the tissue cells. Scattering of excitation radiation is important because if the intensity of the excitation radiation is not sufficiently high, TPF and SHG interactions in the tissue cells will yield emitted light that is too weak to detect.

Nonetheless, imaging through certain types of bone and hard tissue such as cochlear bone from the outside, without entering the cochlea with an endoscope, is of great interest because the cochlea narrows down quickly and the penetration depth is limited by the size of the endoscope. A variety of methods can be used to counteract the scattering of excitation radiation by bone and hard and/or fibrous or membranous tissue. Typically, in such methods, excitation radiation pulses are directed into a spatial light modulator (e.g., spatial light modulator 104), where the temporal, spatial, and/or polarization properties of the pulses are adjusted to compensate for the scattering effects of the bone or hard tissue. Many different techniques are available for adjusting the properties of radiation pulses, and more particularly, to adjust radiation pulses in a manner that specifically compensates for scattering effects in turbid or dense media. Exemplary techniques that can be used in the methods and systems disclosed herein include digital phase conjugation and wavefront optimization. Aspects and features of these techniques are disclosed in the following publications, the contents of each of which is incorporated herein by reference: Z. Yaqoob et al., "Optical phase conjugation for turbidity suppression in biological samples," Nature Photonics 2: 110-115 (2008); I. M. Vellekoop et al., "Exploiting disorder for perfect focusing," Nature Photonics 4: 320-322 (2010); C. L. Hsieh et al., "Imaging through turbid layers by scanning the phase conjugated second harmonic radiation from a nanoparticle," Optics Express 18: 20723-20731 (2010); I. M. Vellekoop et al., "Scattered light fluorescence microscopy: imaging through turbid layers," Optics Letters 35(8): 1245-1247 (2010).

In addition to adjusting the temporal and/or spatial distribution of the excitation radiation based on the light scattering properties of bone and/or other hard tissues, these methods can also be used to compensate for properties of the optical elements used to deliver the excitation radiation to the tissue cells. For example, in some embodiments, the spatial and/or temporal distribution of the excitation radiation can be adjusted to compensate for one or more properties of an endoscope through which the excitation radiation passes. Properties of the endoscope (e.g., the optical fiber(s) within the endoscope) that can be compensated include, for example, light scattering and dispersion.

The use of wavefront shaping methods does not mandate that excitation radiation must be specifically tailored, in a highly detailed way, to the particular bone structure of individual patients when the systems disclosed herein are used in a clinical environment. Although such specific tailoring can certainly be performed, the systems disclosed herein can also access reference libraries that include specifications describing the radiation scattering properties of different types of bone and hard tissue. When the systems disclosed herein are used for in vivo imaging and diagnosis of live patients, suitable excitation radiation spatiotemporal profiles can be determined from library specifications that are close matches for particular patients. In this way, system configuration can be performed in automated fashion by an electronic processor (shown as electronic processor 118), and images of patient tissues can be acquired, displayed for a human technician (on display 119, for example) and rapidly analyzed for diagnostic purposes.

(b) Imaging Through Translucent and Opaque Membranes

The techniques disclosed herein can also be used to image cells, including cells of the inner ear, through fluids that bathe these cells by inserting an endoscope through natural or surgically-made openings into the bone encasing the cells. In addition, in certain embodiments, the methods disclosed herein can be used to image cells without damaging the membranes that cover these openings. For example, the cells can be illuminated, and emitted radiation detected, through the membranes that cover natural openings in the inner ear such as the round window. Using these methods, cochlear cells can be imaged in situ without applying exogenous dyes, by detecting endogenous materials TPF and/or SHG induced in the cells by the excitation light. For example, one such endogenous material is flavin adenine dinucleotide (FAD). Images obtained from measuring TPF and/or SHG signals have high contrast and exhibit cellular, and even subcellular resolution, permitting detection of specific, noise-induced pathologic changes to cochlear tissue.

There are two natural openings into the inner ear: the round and oval windows of the cochlea. The round window is covered by a membrane that is translucent to certain wavelengths of light to varying degrees, but opaque to other wavelengths (e.g., incident light at certain wavelengths is almost completely absorbed by the membrane covering the round window). In particular, the membrane covering the round window is opaque to light in the visible region of the electromagnetic spectrum. The round window membrane includes three layers: a mucous layer facing the middle ear, a middle fibrous layer, and an epithelial layer facing the inner ear. There can also be another opaque "pseudomembrane" in front of the round window membrane. This, imaging through such membranes has been difficult.

Figure 12A:
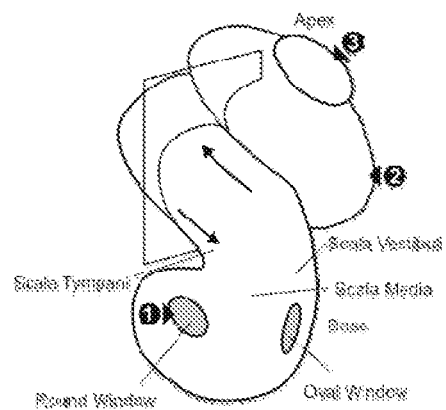
FIG. 12A is a schematic diagram of a cochlea.
Figure 12B:
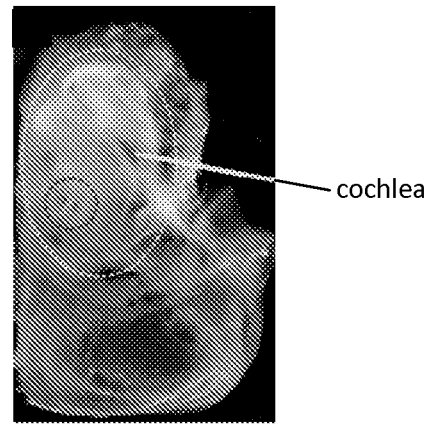
FIG. 12B is a microscope image of a decalcified mouse cochlea.
Figure 12C:
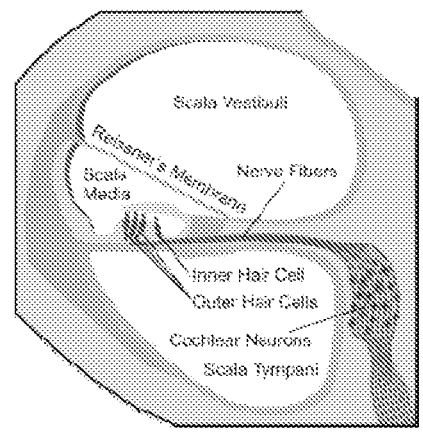
FIG. 12C is a schematic cross-sectional diagram of a cochlea.

The membrane covering the round window oscillates with opposite phase to vibrations entering the inner ear through the oval window, which articulates with the bony stapes. Most hearing loss, including noise-induced and age-related hearing loss, starts and is most prominent in the cochlear region close to the round window. Accordingly, accessing the round window has been of interest for vibratory transducer implants, intra-tympanic drug delivery, and cochlear implants. A schematic diagram of a cochlea is shown in FIG. 12A. The round and oval windows are shown in the lower portion of the figure. FIG. 12B shows an image of a decalcified mouse cochlea (enclosed in a dashed white outline). The round window in FIG. 12B is enclosed in a dark dashed outline. FIG. 12C shows a schematic cross-sectional diagram of the cochlea.

The methods and systems disclosed herein use TPF and SHG to image cochlear tissues at cellular and even subcellular resolution in a minimally invasive manner. The methods can be used to image living or preserved tissues, and can therefore provide important diagnostic and treatment information for therapies to address damage to delicate cochlear cells from excessive noise exposure. Images through the round window membrane, in particular, permit high quality visualization of intracochlear cells, including sensory hair cells and cochlear neurons without exogenous labeling or physically opening the cochlea or rupturing the round window membrane. Imaging without exogenous labeling is particularly significant, because at present the use of exogenous fluorescent dies is highly constrained, and the use of transgenic fluorescent proteins is not yet clinically allowed. Furthermore, it is difficult to introduce exogenous labels into the cochlea without damaging at least the outer surface structure. The methods and systems disclosed herein permit in vivo imaging of cochlear cells without damage to the cells, to the round window or oval window membranes, or to other inner ear tissues.

To image cells through the round window membrane, an endoscope (such as endoscope 202 shown in FIG. 2) is positioned in proximity to the round window membrane, excitation radiation is delivered from the endoscope through the round window membrane to cochlear cells, and emitted light from the cells passes through the round window membrane and is transported by the endoscope to a detector. A variety of methods can be used to position the endoscope in proximity to the round window. For example, in some embodiments, the endoscope can be inserted through a surgically introduced opening in the middle ear, such as a stapedotomy or a cochleostomy. Methods for inserting an endoscope through a cochleostomy opening are described, for example, in U.S. Pat. No. 8,099,156, entitled "Cochlear Optical Analysis System and Approach Therefor," the entire contents of which are incorporated herein by reference.

After positioning the endoscope, the methods for directing excitation radiation to cochlear cells and for detecting emitted TPF and/or SHG radiation from the cells are similar to those disclosed above in connection with through-bone imaging. In general, because the membrane of the round window is thinner and less dense than the bone surrounding the cochlea, scattering of excitation radiation and emitted radiation when imaging through the round window is less significant, and high resolution images can be obtained while employing fewer corrective measures (e.g., adjustment of temporal, spatial, and/or polarization properties of excitation pulses using a spatial light modulator) relative to through-bone imaging.

Nonetheless, the phase conjugation and wavefront shaping techniques disclosed above and herein can also be used when imaging through the round window membrane or other membranous tissue. The round window membrane and the pseudomembrane (if present) scatter illumination radiation, and phase conjugation and wavefront shaping techniques can be used to pre-compensate for such scattering. Further, where an endoscope is used to deliver illumination radiation, the endoscope can introduce distortions including spatial, temporal, and/or polarization distortions of radiation pulses. Phase conjugation and wavefront shaping techniques can be used to compensate for such distortions so that the pulses delivered to the tissue of interest efficiently generate TPF and/or SHG in the tissue.

Applications (a) Diagnostics for Inner Ear Cell Disorders

The systems and methods disclosed herein yield tissue images that can be used for a variety of diagnostic purposes. For example, the high resolution images of individual inner ear cells that are obtained can be used to evaluate the integrity and density of cochlear neurons, the integrity of the organ of Corti and hair cells, the size and cellular density of the spiral ligament, and the size of cochlear chambers. In addition, healthy, neatly arranged hair cells can be distinguished from damaged, disarrayed hair cells.

The methods and systems disclosed herein permit in vivo assessment of cochlear pathology in deaf patients to choose the most appropriate regenerative therapy targeted at specific cells that are missing in a given patient. In addition, diagnostic information available from the images obtained can be used to identify candidate patients for cochlear implants, and facilitate development of optically enhanced cochlear implants to avoid cellular trauma, enhance implant performance, and monitor evolving therapies to be delivered through the implants.

Emitted radiation from different nonlinear optical responses induced in the tissues can be used to interrogate different aspects of the tissues. For example, emitted radiation that arises from SHG in tissues can be used to identify bone, cell boundaries, and certain types of fibers (e.g., collagen) that are birefringent. In contrast, emitted radiation that arises from TPF in tissues (which can include TPF from specific entities within cells and autofluorescence) can be used to diagnose cellular damage (e.g., damaged cells do not fluoresce as strongly as their healthy counterparts), and to distinguish different types of cells which fluoresce at different wavelengths. In addition, the absence of certain types of cells (e.g., inner ear hair cells) can be identified from the absence of emitted TPF radiation. Attributing conditions such as hearing loss to damaged hair cells, rather than the absence of hair cells, can provide valuable information as to the potential for success of proposed regenerative therapies for particular patients.

(b) Diagnostics for Other Types of Tissues

Although the present disclosure focuses particularly on imaging inner ear cells, including imaging through a layer of bone and through membranes that cover natural openings in the inner ear such as the round window, the methods and systems disclosed herein can more generally be applied to imaging of a wide variety of tissues encased in bone, cartilage, and other hard and/or translucent or opaque, scattering tissue layers. In addition, although the methods disclosed herein are particularly useful to imaging unstained cells that are difficult to access (and which might be adversely affected by staining), more generally the methods can also be used to image cells into which various exogenous fluorophores have been introduced. As an example, fluorophores based on gadolinium have been introduced into even certain inner ear cells, and these tagged cells can be imaged at high resolution using the systems and methods disclosed herein.

The methods and systems disclosed herein can also be used to image tissues and cells by using alternate routes to access the inner ear. For example, in some embodiments, an endoscope can be used to image tissues of interest through openings in the inner ear created by a disease condition (e.g., dehiscence of a semicircular canal due to cholesteatoma, infection, tumor, trauma, and/or genetic pathology).

The methods and systems disclosed herein may be used to image components of the vestibular system including otoliths (saccule and utricle) and the semicircular canals (vertical and horizontal). For example, hair cells and nerve fibers of the vestibular system may be used according to the methods described herein. Imaging of vestibular system components may be useful in the diagnosis and/or treatment of vestibular disorders known in the art (e.g., Meniere's disease and vestibular migraine).

In addition to imaging cells of the inner ear (which include cells of the cochlea, saccule, utricle, and 3 semicircular canals (i.e., superior, posterior, and lateral semicircular canals), the methods and systems disclosed herein can be used to image any cells accessible to an endoscope, including cells of the brain, joints, internal organs, bone marrow, and teeth.

(c) Combinations with Other Techniques

The systems and methods disclosed herein can be combined with other methods for tissue imaging. In particular, because both the nonlinear optical imaging methods disclosed herein and OCT are amenable to endoscope implementation, the combination with OCT methods is particularly facile. OCT provides images in which the contrast mechanism is differences in the strength of linear scattering. Nonlinear processing (e.g., using techniques such as TPF and/or SHG) of the signal obtained through OCT can be used to obtain additional information from a variety of tissues. Ultra-short laser pulses can be delivered through the endoscope, so that both OCT and nonlinear images can be obtained using the same radiation source. Further, combining OCT and nonlinear images permits characterization of the health of the cochlea at a single cell level, without any exogenous contrast, thereby allowing for more confident diagnosis and treatment.

(d) Spectral Cell Damage Diagnosis

In addition to providing deep tissue images of cells behind layers of bone and hard tissue, the systems and methods disclosed herein provide spectral information that can be used to diagnose and quantify damage in certain types of cells. FIG. 4A is a graph showing measured TPF spectra from a hair cell region of the cochlea. One of the lines on the graph corresponds to emission from cells that were exposed to 106 dB of white noise in the 8-16 kHz band for a period of 2 hours, and the other line corresponds to emission from cells that were not exposed to noise. The emission spectrum of the exposed cells is significantly broader than the spectrum of the unexposed cells, indicating that damage due to noise exposure has occurred. The increase in spectral width is likely correlated to the amount of damage and the overall fraction of cells that have sustained damage.

Figure 4B:
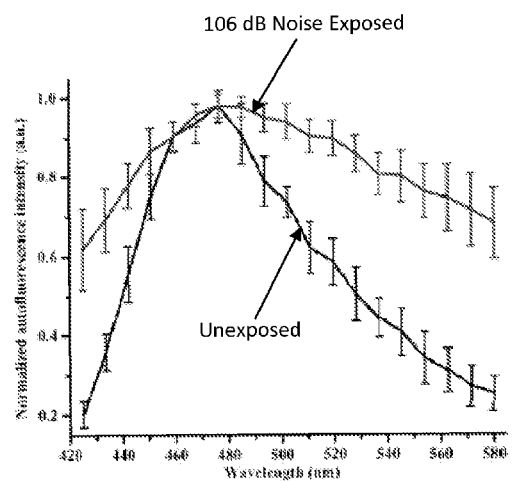
FIG. 4B is a graph showing emission spectra for neuronal cells before and after exposure to traumatic noise.

FIG. 4B is a graph showing similar data for neuronal cells that were exposed (one line) and unexposed (the other line) to the same noise. As in FIG. 4A, the spectral broadening following exposure in FIG. 4B indicates that damage due to excessive noise has occurred among the neurons, providing a reproducible and quantitative diagnostic for inner ear cell damage.

The comparative method illustrated in FIGS. 4A and 4B can generally be used for diagnosis of inner ear cell damage. Determining the bandwidth of the measured emission spectrum for a cell or group of cells, and comparing the determined bandwidth to a reference emission spectrum (e.g., from an experimental control, or from an earlier measurement of the same tissue, or from a library of reference spectra) can provide a determination at to whether one or more inner ear cells are damaged (e.g., if the bandwidth of the measured emission spectrum is larger or smaller than the reference spectrum). Thresholds can be established to determine whether or not a difference between the measured and reference spectral bandwidths are significant. For example, in some embodiments, cells are determined to be damaged if the bandwidth of the measured emission spectrum exceeds or is less than the bandwidth of the reference emission spectrum by 5% or more.

(e) Three-Dimensional Imaging

In systems 100 and 200 disclosed herein, electronic processor 118 can be configured to adjust optical elements such as lenses and endoscopes to direct excitation radiation to particular locations within tissues of interest. For example, the location to which excitation radiation is delivered can be controlled along three orthogonal coordinate axes, so that particular portions of tissue can be selectively interrogated. Because TPF is generated only at the spatiotemporal peak of incident radiation pulses, this selective control can be used for three-dimensional tissue imaging. To obtain a three-dimensional tissue image, a first image is obtained by imaging a planar thickness of tissue along two coordinate directions. Next, the focal point of the excitation radiation is translated in a direction orthogonal to the first plane, to a new planar thickness of the same tissue. The new planar thickness of tissue is imaged along the same two coordinate directions. The process is repeated to obtain a stack of two-dimensional images, each corresponding to a different "slice" through the tissue of interest.

In some embodiments, the stack of two-dimensional images can be combined to form a three-dimensional images. A variety of different methods can be used to combine such images. For example, images can be combined using a maximum intensity projection (MIP) algorithm. MIP algorithms are disclosed, for example, in Wallis et al., "Three-dimensional display in nuclear medicine, *IEEE Trans. Med. Imaging* 8(4): 297-303 (1989), the entire contents of which are incorporated herein by reference.

Hardware and Software

The method steps and procedures described herein can be implemented in hardware or in software, or in a combination of both. In particular, electronic processor 118 can include software and/or hardware instructions to perform any of the method steps disclosed above. The methods can be implemented in computer programs using standard programming techniques following the method steps disclosed herein. Program code is applied to input data to perform the functions described herein. The output information is applied to one or more output devices such as a printer, or a display device, or a web page on a computer monitor with access to a website, e.g., for remote monitoring.

Each program is preferably implemented in a high level procedural or object oriented programming language to communicate with a processor. However, the programs can be implemented in assembly or machine language, if desired. In any case, the language can be a compiled or interpreted language. Each computer program can be stored on a storage medium or device (e.g., an electronic memory) readable by the processor, for configuring and operating the processor to perform the procedures described herein.

Interfaces that can be used to display images include a wide variety of displays (e.g., CRTs, LED-based displays, liquid crystal-based displays, projection displays). Interfaces can be touch-sensitive, allowing a user to interact directly with the displayed elements. Alternatively, or in addition, additional system components (e.g., keyboards, pointing devices) can permit a user to manipulate elements displayed on the interface.

EXAMPLES

The subject matter disclosed herein is further described in the following examples, which are not intended to limit the scope of the claims.

Example 1—Through-Bone Imaging of Neurons

Figure 5:
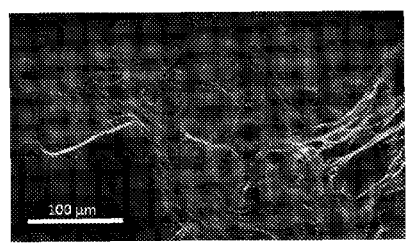
FIG. 5 is an image of two-photon fluorescence from mouse cochlear neurons.

Mouse cochleas obtained from sacrificed laboratory animals were first imaged using the methods and systems disclosed herein to explore the feasibility of obtaining images of inner ear neurons without staining the cochlear tissue. FIG. 5 shows an example of an image of TPF from mouse cochlear neurons. In particular, the neurons in FIG. 5 are unstained; emission arises only from endogenous fluorophores within the cells. Excitation (illumination) radiation was transmitted directly through the mouse cochlear bone to reach the neuronal cells. The example in FIG. 5 shows that high resolution images of neurons can be obtained directly through the bone encasing the cochlea without staining the neurons.

Example 2—Through-Bone Imaging of Cochlear Cells and Tissue

To explore a variety of aspects of the methods disclosed herein, mouse and human cochleas were prepared for imaging. Mice (8 week old CBA/CaJ mice) were perfused with paraformaldehyde and their cochleas extracted as described, for example, in K. Stankovic et al., "Survival of adult spiral ganglion neurons requires erbB receptor signaling in the inner ear," Journal of Neuroscience 24: 8651-8661 (2004), the entire contents of which are incorporated herein by reference. Human temporal bones were obtained fixed in formaldehyde. The bones were prepared for imaging using standard surgical approaches to the inner ear, including tympanostomy, canal wall up mastoidectomy with facial recess approach, and/or canal wall down mastoidectomy.

The prepared cochleas were then imaged ex vivo by confocal microscopy and endoscopy to obtain OCT, TPF, and SHG images. FIG. 6A shows an image of a mouse cochlea, and FIG. 6B shows an image of a human cochlea obtained using a confocal microscope at an excitation wavelength of 800 nm. The inside of the cochlea is plainly visible in each image, even though imaging was performed directly through the cochlear bone. Imaging contrast in FIGS. 6A and 6B relies on intrinsic linear scattering and nonlinear phenomena including autofluorescence and endogenous SHG signals from the cells and structures of the cochlea.

FIGS. 7, 8A-8B, 9A-9B, 10A-10B, and 11A-11B show additional images of inner ear cells imaged at varying magnifications. FIG. 7 shows a nine week old normal cochlea. In FIG. 7, the basal turn is imaged directly through the encasing bone. The image in FIG. 7 includes contributions from both autofluorescence and SHG in the tissue.

Figure 8A:
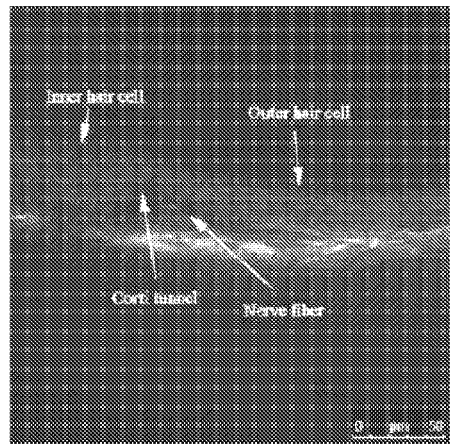
Figure 8B:
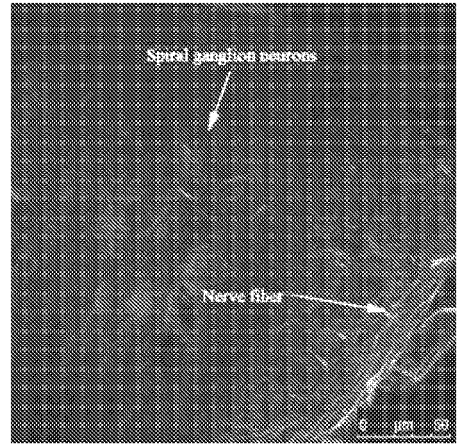

FIGS. 8A and 8B also show images of a nine week old normal cochlea imaged through the encasing bone. A variety of structural entities are visible and labeled in FIG. 8A. FIG. 8B is a higher magnification image that shows individual spiral ganglion neurons and nerve fibers.

Figure 9A:
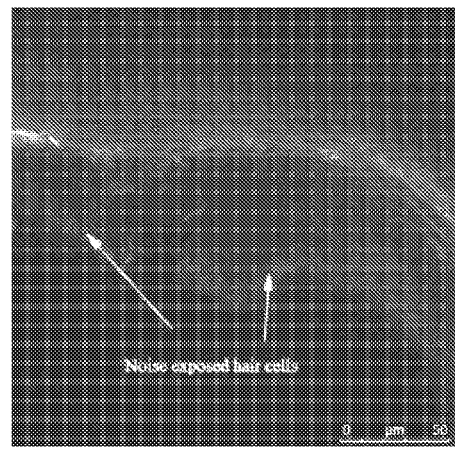
FIGS. 9A and 9B are images of a nine week old cochlea 3 weeks after exposure to traumatic noise.
Figure 9B:
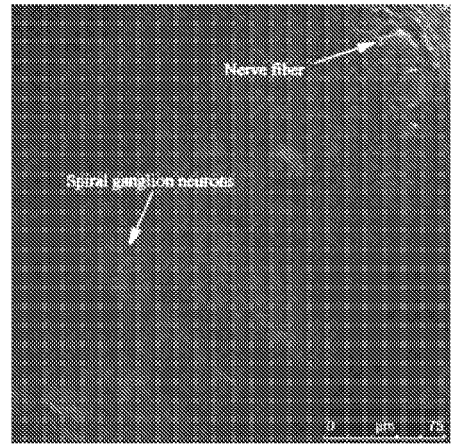

FIGS. 9A and 9B show lower and higher magnification images, respectively, of a nine week old cochlea 3 weeks after exposure to traumatic noise (106 dB of white noise in the 8-16 octave kHz band for 2 hours). Once again, the basal turn was imaged through the encasing bone. The images in FIGS. 9A and 9B include contributions from both autofluorescence and SHG. As is evident particularly in FIG. 9A, cells damaged by noise exposure are torn away from the basilar membrane.

Figure 10A:
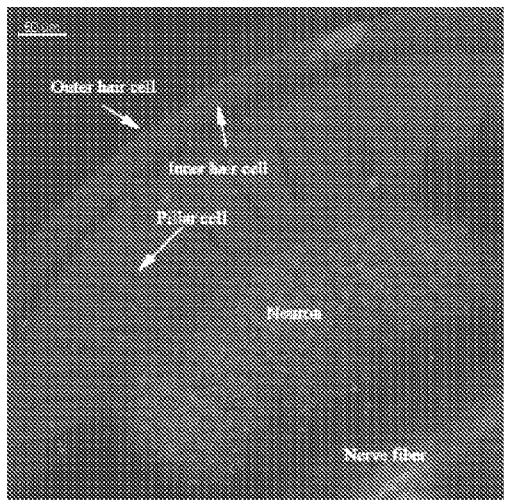
FIGS. 10A and 10B are images of a nine week old normal cochlea where the apical turn is imaged following decalcification.
Figure 10B:
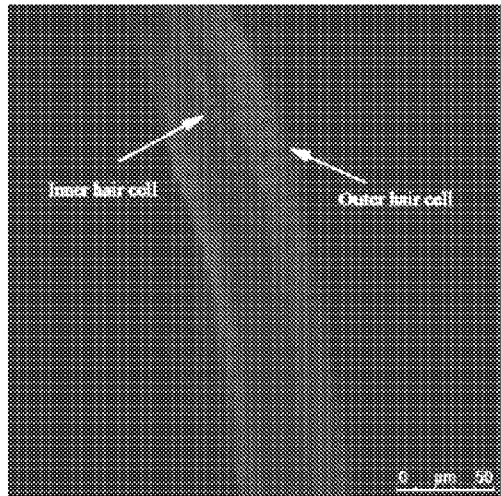

FIGS. 10A and 10B show lower and higher magnification images, respectively, of a nine week old normal cochlea, where the apical turn is imaged following decalcification. A variety of structures are visible in the image, including individual inner and outer hair cells, neurons, and nerve fibers.

Figure 11A:
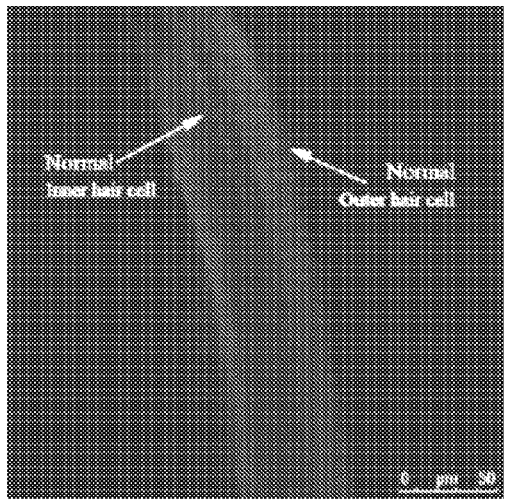
FIG. 11A is an image of a nine week old normal cochlea.
Figure 11B:
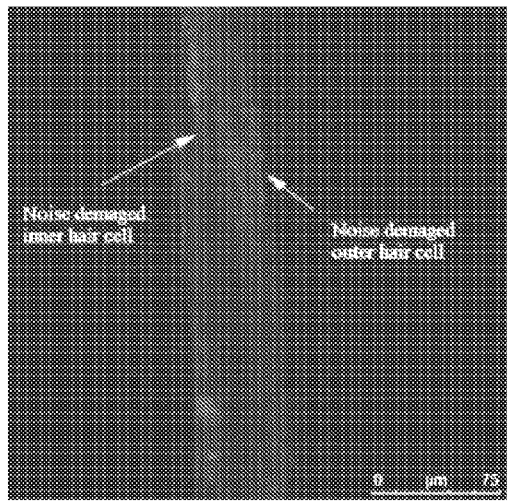
FIG. 11B is an image of the same cochlea as in FIG. 11A three weeks after exposure to traumatic noise.

FIG. 11A shows an image of a nine week old normal cochlea, and FIG. 11B shows an image of the same cochlea 3 weeks after exposure to traumatic noise (106 dB of white noise in the 16-18 kHz band for 2 hours) for comparison. The apical turn of the cochlea is imaged after decalcification in each image. Comparing FIGS. 11A and 11B, it is evident that both noise damaged inner hair cells and noise damaged outer hair cells in FIG. 11B are swollen relative to their unexposed counterparts in FIG. 11A.

The results shown in FIGS. 6A-6B, 7, 8A-8B, 9A-9B, 10A-10B, and 11A-11B show that high resolution images of cochlear tissues can be obtained directly through the encasing bone surrounding the cochlea, and that such images can readily be used to identify noise-induced trauma in the tissues.

Example 3—Imaging of Tissues Through Membranes

To evaluate imaging of cochlear tissues through the round window membrane to assess damage to inner ear cells from acoustic overexposure, six week old male mice (N=12) of the CBA/CaJ strain were exposed to an octave band noise of 8-16 kHz at 106 dB sound pressure level (SPL) for 2 hours. This level of noise is known to cause permanent cellular damage, which is maximal close to the round window, and decreases from cochlear base to apex. Animals were unrestrained during noise exposure within cells in a subdivided cage (1 animal/cell). The cage was suspended in a small, reverberant chamber, directly below the horn of the sound-delivery loudspeaker. Noise calibration to target SPL was performed immediately before each exposure session. Unexposed age- and sex-matched mice served as controls (N=12).

The noise-exposed and control mice were sacrificed two weeks after the exposure to allow the wound in the acoustically traumatized organ of Corti to heal so as to bring out permanent, irreversible changes. This mimics the condition that is typically encountered in clinic, where patients manifest permanently wounded rather than freshly-wounded cochleae. The animals were intracardially perfused with 4% paraformaldehyde in 0.1 M phosphate buffer. The left inner ears were extracted, stored in 4% paraformaldehyde at room temperature, and imaged within a week of harvest to ensure a strong signal. The right inner ears were removed, post-fixed, decalcified in 0.1 M EDTA, dehydrated, embedded in paraffin, serially cut (10 µm thickness) and mounted on microscope slides. Select ears were stained with 1% osmium tetroxide prior to decalcification, embedded in Araldite® and serially sectioned (20 µm thickness). A separate group of 8-week old unexposed animals (N=10) was sacrificed and their cochleae were extracted without using intracardiac or intracochlear fixatives. These unstained cochleae were imaged within 5 minutes of extraction to determine endogenous TPF without chemical fixatives.

Intracochlear structures were imaged through the round window in situ by detecting TPF from the structures. The cochlea were neither opened nor sliced. To prepare the cochlea for imaging, the extracted left inner ears were mounted in an elastic mould made of 1% agarose in water, and oriented with the round window facing the microscope objective.

The TPF images were acquired using a Leica® SP5 multiphoton microscope system (available from Leica Microsystems, Buffalo Grove, Ill.) equipped with a mode-locked Ti:Sapphire laser (Coherent Chameleon, available from Coherent, Inc., Santa Clara, Calif.) as the light source. The excitation wavelength was 812 nm and the pulse width was 140 fs. TPF and SHG signals were collected in a reflective configuration through the same microscope objective (Leica HCX APO 20×1.0 water immersion). After a 680-nm short-pass filter to eliminate the excitation light, the signals were sent to two photomultiplier tubes (PMTs) for simultaneous TPF and SHG detection through band-pass filters centered at 525 nm (50 nm bandwidth) and 406 nm (10 nm bandwidth), respectively. The average excitation power measured at the focal plane was about 10 mW, resulting in a peak intensity of approximately $9 \times 10^{11}$ W/cm$^2$. The pixel dwell time was chosen between 2 µs and 8 μs according to the signal intensity from different samples. For all images, intensities were averaged over 8 consecutive frames.

The TPF images were compared with images obtained using a Zeiss® LSM 700 microscope in both one-photon fluorescence confocal mode and wide-field transmission mode. In the confocal mode, the excitation wavelength was 405 nm, and the emission wavelength was 515-565 nm. In both imaging modes, the objective used was a Zeiss® N-achromat 20×0.5 NA water immersion objective.

Figure 13A:
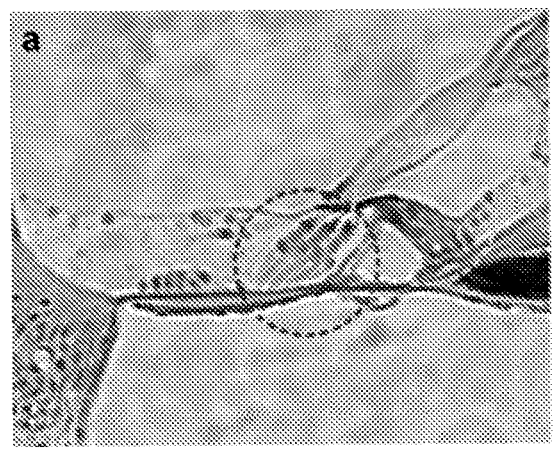
FIG. 13A is a wide-field transmission microscopy image of an osmium-stained section of an inner ear.
Figure 13B:
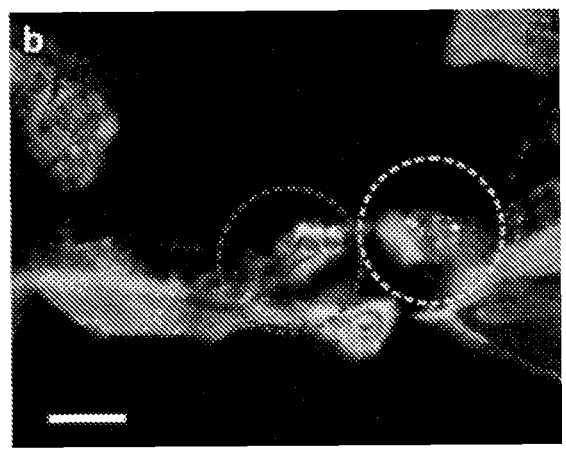
FIG. 13B is a two-photon fluorescence image of an unstained inner ear section similar to the section of FIG. 13A.

To evaluate the effectiveness of TPF as an intrinsic contrast for the imaging of the organ of Corti, TPF images of a paraffin-embedded histologic section (e.g., right ears of the sacrificed animals) were obtained and compared to wide-field transmission microscopy images of a similarly oriented, osmium-stained section. FIG. 13A shows a wide-field transmission microscopy image of an osmium-stained section of an inner ear (showing the organ of Corti), and FIG. 13B shows a TPF image of a similarly-positioned unstained inner ear section. In FIG. 13A, the pixel size is 375 nm. In FIG. 13B, the pixel size is 170 nm and the scale bar is 10 μm. The main structures of interest, namely the inner and outer hair cells (marked by the dashed circles) are clearly revealed in the TPF image.

Figure 14A:
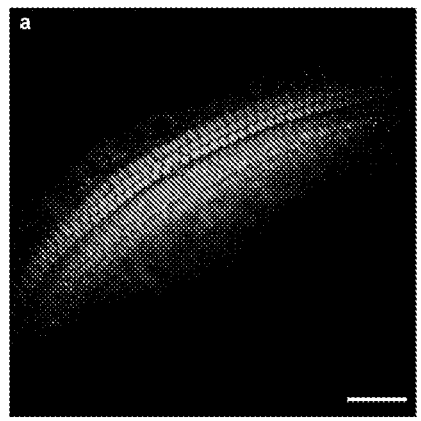
FIG. 14A is a two-photon fluorescence image of cochlear tissue obtained by imaging through the round window.
Figure 14B:
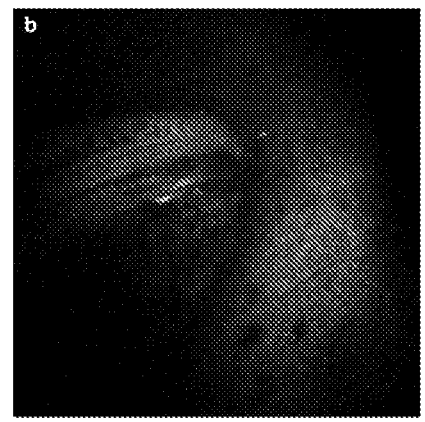
FIG. 14B is a one-photon fluorescence image of the sample of FIG. 14A.
Figure 14C:
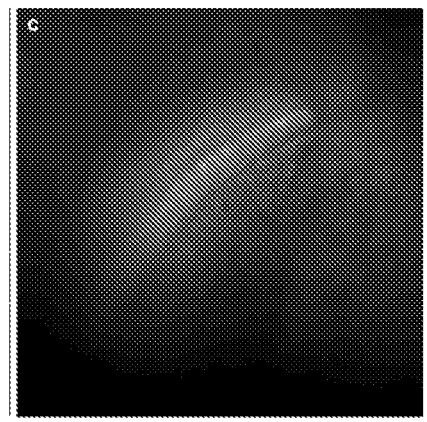
FIG. 14C is a wide-band transmission microscopy image of the sample of FIG. 14A.

TPF images of the intrachochlear structures in situ were then obtained by imaging the structures through the intact round window membrane (e.g., the left ears of the sacrificed animals) in situ, without decalcifying or sectioning the cochlea prior to imaging. FIG. 14A shows an exemplary TPF image of the organ of Corti obtained by imaging through the round window. FIGS. 14B and 14C show images of the same structure obtained using one-photon fluorescence confocal microscopy and wide-band transmission microscopy, respectively.

The resolution of the images in FIGS. 14A and 14B is approximately 350 nm, while the resolution of the image in FIG. 14C is approximately 375 nm. The scale bar in FIG. 14A is 50 μm, and the pixel sizes are 170 nm in FIGS. 14A and 14B, and 375 nm in FIG. 14C. Rows of hair cells are observed with high resolution in FIG. 14A. However, the image in FIG. 14B shows less detail and a lower signal-to-noise ratio (SNR), likely due to the linear dependence of excitation/emission in one-photon microscopy. The wide-field transmission image in FIG. 14C is blurry, likely due to the lack of axial resolution (optical sectioning) and strong scattering from the surrounding bone. The image contrast, defined as the ratio of the mean intensity of the hair cell region to the mean intensity of the imaging plane 10 μm above the hair cell, is approximately 4 for the image in FIG. 14A and approximately 2 for the image in FIG. 14B. The SNR, defined as the ratio of the mean intensity of the hair cell region to the standard deviation of the background in the peripheral area of the same imaging plane, is approximately 20 for the image in FIG. 14A and approximately 10 for the image in FIG. 14B.

In FIGS. 14A-C, the organ of Corti region is about 500 μm below the plane of the round window. The round window opening has a diameter of about 700 μm. The resulting viewing angle onto the organ of Corti through the round window is approximately ±44°. The collection angles of the objectives used for the images in FIGS. 14A and 14B are about ±49° and about ±25°, respectively. The objective used to obtain the image in FIG. 14A was better than the objective used to obtain the image in FIG. 14B with regard to the efficiency of signal light collection. This might also contribute to the dimmer signal in the image of FIG. 14B. However, since measured signal levels in all three images were much stronger than the level of detector noise, it is believed that the optical sectioning capability of TPF imaging is the major contributor to the enhanced image quality compared to one-photon fluorescence imaging.

Example 4—Imaging of Unfixed Cochlear Tissues

The images shown in FIGS. 14A-C were obtained from fixed cochlear samples. An advantage of fixed samples is that tissue degradation is halted so that imaging approaches can be developed and optimized ex vivo before eventual studies in vivo. Although the paraformaldehyde fixative that were used are known to be superior to other fixatives in preserving cell fluorescence while limiting background fluorescence, the fixative can nonetheless fluoresce when exposed to radiation. To determine if the recorded TPF was indeed endogenous and not accidental due to the fixative, freshly harvested, unfixed cochleae—removed from laboratory specimens as described above—were imaged through the round window membrane. An image of the organ of Corti obtained within 5 minutes of cochlear extraction is shown in FIG. 15. In FIG. 15, the scale bar is 10 μm and the pixel size is 170 nm. The image shows the same hair cell structures as observed in the fixed samples shown in FIGS. 14A-C from a different viewing angle. The intensity of the fluorescence is brighter in the freshly harvested, unfixed samples than in the fixed samples. It was therefore concluded that the observed TPF in fixed samples is attributable primarily to endogenous TPF.

FIGS. 16A-H show TPF images of the organ of Corti in a fixed sample, obtained by imaging through the round window of an intact cochlea. To better visualize the overall 3D structure, a stack of images were obtained in a volume and then rendered using maximum intensity projection (MIP) when necessary. This simple approach revealed clear distinctions between healthy and noise-damaged organ of Corti structures. The images were obtained at the location denoted by the numeral "1" in FIG. 12A. FIG. 16A shows a MIP of the 3D image stack of the entire hook region. FIGS. 16B-D show images of three selected planes with 10 μm distance from each other. TPF from most cellular tissues exhibits strong contrast, based on which the hair cells and the supporting cells are clearly identifiable. Due to its weak intrinsic fluorescence, the stereocilia on the apical surface of the hair cell are not visible in the images. The appearance and quality of the TPF images is similar to the images of cochlear whole-mounts, even though the images were acquired from intact cochleae through the round window membrane, demonstrating that an important feature of the methods and systems disclosed herein is that high resolution images of the organ of Corti can be obtained through the round window membrane of an intact cochlea without the invasiveness and terminal nature of whole mount preparations. Signals from SHG likely arise from myelin sheath surrounding neuronal axons that course between neuronal somata.

Noise-exposed cochleae were imaged in the same orientation for comparison. FIG. 16E is a maximum intensity projection (MIP) of a 3D image stack of the entire hook region. FIGS. 16F-H show images of three selected planes with 10 μm distance from one another. Substantial damage and loss of hair cells are evident in the images after noise exposure. Outer hair cells (indicated by asterisks), which are known to be most sensitive to noise trauma, are missing altogether in FIGS. 16G and 16H, while inner hair cells (indicated by arrowheads) are decimated in the same figures. The SNR for each of these images is approximately 20.

Example 5—Imaging Neurons Through Cochlear Bone

As described in greater detail previously, TPF microscopy can also be used to image cochlear neurons at the cellular level through the encasing cochlear bone instead of through the round window. FIG. 17 shows a TPF image of cochlear neurons obtained by imaging a sample cochlea, obtained from a laboratory specimen as described above, directly through the cochlear bone. The image shows neural somata, the average size of which is approximately 20 µm (e.g., approximately 5 times bigger than the hair cells). Small amounts of SHG signal in FIG. 17 may originate from the myelin sheath of the cochlear nerve fibers (indicated by arrowheads). Detection of this SHG signal can provide information for the diagnosis of hearing problems that have a neural origin.

A major endogenous fluorophore in the inner ear is flavin adenine dinucleotide (FAD), whose fluorescence emission peak (approximately 520 nm) coincides with the TPF signal that was measured in the experiments described herein. This, in combination with the fact that the sensory epithelium of the inner ear has one of the highest tissue concentrations of flavin adenine dinucleotide known, shows that TPF imaging can be used to provide important information for cellular diagnosis of sensorineural hearing loss.

Example 6—Detection of Sensorineural Damage in Basal and Apical Cochlear Turns

Imaging through the round window membrane is particularly well suited to provide diagnostic information about the hook region of the organ of Corti, which is the most probable place for initiation of sensorineural damage. However, the methods and systems disclosed herein can also be used to provide information about other cochlear regions as well, including the basal and apical cochlear turns. To assess noise-induced damage along the length of the cochlea, the cochlear bone was decalcified in a selection of samples using 80% formic acid and 20% tri-sodium citrate for 3 hours. After decalcification, through-bone TPF images of the basal and apical cochlear turns were obtained. It was observed that the penetration depth in the TPF images improved from approximately 100 µm to approximately 2 mm following decalcification (and was ultimately limited by the working distance of the microscope objective).

Images of the upper basal turn were obtained by imaging at the brain side of the cochlea (e.g., the location denoted by numeral "2" in FIG. 12A. FIGS. 18A and 18C show the MIP of image stacks obtained at the upper basal turn for normal and noise exposed cochleae, respectively. FIGS. 18B and 18D show high-magnification images of the same regions. Cellular-level details of the organ of Corti are clearly discernible. Noise exposure leads to less cellular damage in the upper basal turn compared to the hook region, which is consistent with the parameters of the acoustic overexposure that was introduced. Although outer hair cells are disarrayed after noise trauma (denoted by asterisks in FIGS. 18B and 18D), only a small portion of them are torn off from the basilar membrane in the upper basal turn.

Images of the apical turn of the decalcified cochlea were obtained by imaging at the location denoted by numeral "3" in FIG. 12A, with samples oriented with the apex of the cochlea perpendicular to the microscope objective. FIGS. 19A and 19C show the MIP of image stacks obtained at the apical turn for normal and noise exposed cochleae, respectively. FIGS. 19B and 19D show high-magnification images of the same regions. In FIGS. 19A-D, no noise-induced loss of hair cells (denoted by asterisks) is apparent, which is consistent with the parameters of the acoustic overexposure that was introduced.

Other Embodiments

A number of embodiments have been described. Nevertheless, it will be understood that various modifications may be made without departing from the spirit and scope of the disclosure. Accordingly, other embodiments are within the scope of the following claims.

What is claimed is:

1. A method for imaging ear tissue, the method comprising:
without contacting a round window membrane of a cochlea comprising the ear tissue, directing illumination radiation to pass through the round window membrane and be incident on ear tissue that does not comprise an exogenous fluorophore at a plurality of locations, the illumination radiation comprising a plurality of light pulses each having a temporal duration of 500 femtoseconds or less;
for each one of the plurality of locations, using a detector to detect radiation emitted from the location that passes through the round window membrane; and
forming an image showing at least one of inner ear neurons and inner ear hair cells of the tissue based on the detected radiation at each of the plurality of locations,
wherein the emitted radiation corresponds to endogenous two-photon fluorescence of the tissue.

2. The method of claim 1, wherein the radiation emitted by the tissue comprises radiation produced by harmonic conversion of the incident radiation.

3. The method of claim 2, further comprising, prior to illuminating the tissue, selecting a central wavelength of the illumination radiation to increase an efficiency of the harmonic conversion of the incident radiation, relative to an efficiency of harmonic conversion of the incident radiation induced by uniform exposure to a band of wavelengths from 400 nm to 800 nm.

4. The method of claim 1, further comprising, prior to illuminating the tissue, selecting a central wavelength of the illumination radiation to increase an efficiency of the endogenous two-photon fluorescence of the tissue, relative to an efficiency of two-photon fluorescence emission induced by uniform exposure to a band of wavelengths from 400 nm to 800 nm.

5. The method of claim 1, further comprising:
positioning an endoscope proximal to the round window membrane;
using the endoscope to deliver the illumination radiation to the round window membrane; and
using the endoscope to collect the emitted radiation emerging through the round window membrane, and to transport the emitted radiation to the detector.

6. The method of claim 1, further comprising:
identifying hair cells in the image; and
determining whether acoustically-induced damage has occurred in the tissue based on the identified hair cells.

7. The method of claim 1, further comprising:
identifying a cell in the image;

measuring a spectrum of a portion of the emitted radiation corresponding to the cell to generate a measured emission spectrum for the cell;

comparing the measured emission spectrum to a reference two-photon fluorescence emission spectrum for an undamaged cell; and determining whether the cell is damaged based on the comparison between the spectra.

8. The method of claim 7, wherein the comparing comprises determining a bandwidth of the measured emission spectrum, and comparing the determined bandwidth to a bandwidth for the reference emission spectrum.

9. The method of claim 1, further comprising:

repeating the steps of the method of claim 1 to form a plurality of successive images of the tissue;

after forming each one of the successive images, directing the illumination radiation to a different plurality of locations so that a next one of the successive images comprises contributions from a different region of the tissue; and combining the plurality of successive images to form a three-dimensional image of the tissue.

10. The method of claim 1, further comprising:

identifying a plurality of cells of the tissue in the image; and determining whether each one of the cells is a neuron or a hair cell based on a central wavelength of a portion of the emitted radiation corresponding to the cell.

11. The method of claim 8, further comprising determining that the cell is damaged if a difference between the bandwidths of the measured and reference emission spectra is 5% or more.

* * * * *